US008486863B2

(12) United States Patent
Audenaert et al.

(10) Patent No.: US 8,486,863 B2
(45) Date of Patent: Jul. 16, 2013

(54) ACTIVATORS OF LATERAL ROOT FORMATION

(75) Inventors: Dominique Audenaert, Opbrakel (BE); Tom Beeckman, Merelbeke (BE); Bert De Rybel, Nieuwerkerken (BE); Dirk G. Inze, Moorsel-Aalst (BE)

(73) Assignees: VIB VZW, Gent (BE); Universiteit Gent, Gent (BE)

( * ) Notice: Subject to any disclaimer, the term of this patent is extended or adjusted under 35 U.S.C. 154(b) by 821 days.

(21) Appl. No.: 12/312,571

(22) PCT Filed: Nov. 22, 2007

(86) PCT No.: PCT/EP2007/062684
§ 371 (c)(1),
(2), (4) Date: Dec. 4, 2009

(87) PCT Pub. No.: WO2008/062035
PCT Pub. Date: May 29, 2008

(65) Prior Publication Data
US 2010/0105561 A1    Apr. 29, 2010

(30) Foreign Application Priority Data
Nov. 23, 2006  (EP) ................................. 06124685

(51) Int. Cl.
A01N 43/10    (2006.01)
A01N 43/26    (2006.01)
A01N 43/16    (2006.01)
A01N 43/08    (2006.01)

(52) U.S. Cl.
USPC ........... 504/289; 504/290; 504/292; 504/294; 504/299

(58) Field of Classification Search
None
See application file for complete search history.

(56) References Cited

U.S. PATENT DOCUMENTS

| 4,297,125 A | 10/1981 | Haissig et al. |
| 4,411,684 A | 10/1983 | Boyles et al. |
| 4,415,350 A | 11/1983 | Boyles et al. |

FOREIGN PATENT DOCUMENTS

| DE | 35 24 334 A1 | 1/1986 |
| DE | 3524334 | 1/1986 |
| DE | 38 22 501 | 1/1990 |
| DE | 3822501 | 1/1990 |
| EP | 0 009 324 | 4/1980 |
| EP | 0 009 324 a1 | 4/1980 |
| EP | 0 048 998 | 4/1982 |
| EP | 0 048 998 A2 | 4/1982 |
| EP | 0048998 * | 4/1982 |
| EP | 0 092 730 | 4/1983 |
| EP | 0 092 730 A | 11/1983 |
| EP | 0 199 658 | 10/1986 |
| EP | 0 199 658 A1 | 10/1986 |
| EP | 0199658 * | 10/1986 |
| WO | WO 2008/062035 A2 | 5/2008 |

OTHER PUBLICATIONS 2, 4-DEP data Sheet; http://www.alanwood.net/pesticides/2,4-dep.html; taken from website Apr. 19, 2007.
Burkhanova et al.; Comparative Study of the Effects of 6 Benzylaminopurine Thidiazuron and Cartolin on Growth of Intact Pumpkin Seedlings; Biosis / Biosis ; 1984.
Kakiuchi et al.; Synthesis and lateral root-inducing activity of 3-hydroxymethyl-2-substituted-4-butanolides; Journal of the Faculty of Agriculture, 2000; 45(1); 125-133.
Synthetic Pesticides (Ecotoxicology); PubMed; Apr. 19, 2007; 52 pages.
Kakiuchi et al., Synthesis and lateral root-inducing activity of 3-hydroxymethyl-2-substituted-4-butanolides. Journal of the Faculty of Agriculture, Kyushu University, Japan, 2000, pp. 125-133. vol. 45, No. 1.
Kurkhanova et al., Comparative Study of the Effects of 6 Benzylaminopurine Thidiazuron and Cartolin on Growth of Intact Pumpkin Seedlings, Biosciences Information Service, 1984, pp. 13-19. vol. 31, No. 1.
Synthetic Pesticides, Internet Article. <http://web.archive.org/web/20050210452​51/http://focosi.altervista.org/pesticides.html>
retrieved on Apr. 19, 2007, p. 28.
Pesticides, 2,4-DEP Data sheet, Internet Article, <http://www.alanwood.net/pesticides/2,4-dep.html>, retrieved on Apr. 19, 2007.
PCT International Search Report, PCT/EP2007/062684, dated May 19, 2008.
U.S. Appl. No. 10/666,778, filed Sep. 18, 2003, Goossens et al., The Use of Genes Encoding Membrane Transporter Pumps to Stimulate the Production of Secondary Metabolites in Biological Cells.
U.S. Appl. No. 11/225,709, filed Sep. 12, 2005, Inze et al., A Method for Protein Cleaving Using a Metacaspase Polypeptide.
U.S. Appl. No. 11/660,483, filed Apr. 22, 2008, Cnops et al., Modulation of Plant Cell Number.
U.S. Appl. No. 11/992,030, filed Mar. 14, 2008, Goossens et al., Means and Methods to Enhance the Production of Vinblastine and Vincristine in *Catharanthus roseus*.
U.S. Appl. No. 12/311,683, filed Apr. 8, 2009, Audenaert et al., Non-Steroidal Brassinosteroid Mimetic.
U.S. Appl. No. 61/190,543, filed Aug. 29, 2008 De Jaeger et al., The AN3 Protein Complex and Its Use for Plant Growth Promotion.
U.S. Appl. No. 61/206,795, filed Feb. 3, 2009, Goossens et al., Genes and Uses Thereof to Modulate Taxane Biosynthesis.

* cited by examiner

*Primary Examiner* — Alton Pryor
(74) *Attorney, Agent, or Firm* — TraskBritt

(57) ABSTRACT

The present invention relates to small chemical compounds that act as activators of lateral root formation in plants. More specifically, it relates to small chemical compounds that are structurally not related to auxin but do have a similar effect on root density development in plants. Preferably, these compounds act more specifically on root development than auxin, and may have a different working mechanism.

4 Claims, 54 Drawing Sheets

A1

A2

A3

A4

A5

A6

A7

A8

A9

A10

A11

A12

A13

A14

A15

A16

A17

A18

A19

A20

A21

A22

A23

A24

A25

A26

A27

A28

A29

A30

A31

A32

A33

A34

A35

A36

A37

A38

A39

A40

A41

A42

A43

A44

A45

A46

A47

A48

A49

A50

A51

A52

A53

A54

A55

A56

A57

A58

A59

A60

A61

A62

A63

A64

A65

A66

A67

A68

A69

A70

A71

A72

A73

A74

A75

A76

A77

A78

A79

A80

A81

A82

A83

A84

A85

A86

A87

A88

A89

A90

A91

A92

A93

A94

A95

A96

A97

A98

A99

A100

A101

A102

A103

A104

A105

A106

A107

A108

A109

A110

A111

A112

A113

A114

A115

A116

A117

A118

A119

A120

A121

A122

A123

A124

A125

A126

A127

A128

A129

A130

A131

A132

A133

A134

A135

A02

A02 VAR1

A02 VAR2

A02 VAR3

A02 VAR4

A02 VAR5

A02 VAR6

A11

A11 VAR1

A11 VAR2

A11 VAR3

A11 VAR4

A11 VAR5

A14

A14 VAR1

A14 VAR2

A14 VAR3

A14 VAR4

A14 VAR5

ACTIVATORS OF LATERAL ROOT FORMATION

The present invention relates to small chemical compounds that acts as activators of lateral root formation in plants. More specifically, it relates to small chemical compounds that are structurally not related to auxin but do have a similar effect on root density development in plants. Preferably, these compounds act more specifically on root development than auxin, and may have a different working mechanism.

In plants, the formation of lateral roots (LRs) is a crucial step in the development of the root system. LRs do not only provide stable anchorage of the plant, but they also contribute to an efficient water use and uptake of nutrients from the soil. The key regulator of lateral root (LR) development is the phytohormone auxin, which plays a central role in the initiation and outgrowth of LRs (Casimiro et al., 2003).

Auxins are a class of plant hormones including indole-3-acetic acid (IAA), 4-chloro indole acetic acid, indole-3-butiric acid and 2-phenylacetic acid. Due to their importance in plant development, and the fact that the most active auxin, IAA, is labile in aqueous solution and cannot be applied commercially as plant growth regulator, several synthetic auxin-like compounds have been developed such as 1-naphtalene acetic acid, 2,4-dichlorophenoxyacetic acid and 2,4,5-thrichlorophenoxyacetic acid. All these compounds are based on an indol, a naphthalene or a single phenoxy core, which is probably important in the recognition by the auxin receptor. Several of these compounds have been disclosed in patents, such as U.S. Pat. No. 4,411,684 en U.S. Pat. No. 4,415,350.

Beside the development of lateral roots, auxin mediates also other developmental processes such as new leaf formation, vascular tissue development and floral primordia initiation (Fleming 2005; Teale et al., 2006; Weiss et al., 2005). Consequently, the addition of auxin to plants induces a range of pleiotropic effects, which makes auxin less applicable as a specific activator of LR development. Furthermore, auxin acts in a threshold-like mechanism and is therefore less tunable because small variations in auxin concentrations can have major phenotypic differences.

The density of the lateral roots is important in plant development and plant biomass production. Increasing the number of LRs leads to enhanced lateral branching of the root system and gives the plant a more stable anchorage in the soil. Furthermore, nutrient uptake will be improved, which could lead to an increase in biomass production. Therefore, the development of additional chemical compounds that can stimulate lateral root development, preferably without interaction with the auxin receptor is important.

Surprisingly we found that chemical compounds without the canonical auxin like structure, consisting of an indol, naphthalene or single phenoxy core do have lateral root promoting activity, without interacting with the auxin receptor TIR1.

A first aspect of the invention is the use of a chemical compound comprising at least one aromatic C six-membered ring and a C six-membered ring or a heterocyclic five-membered ring, whereby none of said C six-membered ring structures are linked in a bicyclic structure, to promote lateral root growth in plants. Said structure doesn't comprise a naphthalene core nor an indole core; in case of a phenoxy core a second ring structure is present, distinguishing those compounds from the known auxin like compounds. Preferably, said structure comprises at least one aromatic C six membered ring and a C six membered ring. The second C six-membered ring and the heterocyclic five-membered ring may be aromatic or not. Preferably, the aromatic C six-membered ring is halogenated. Preferably, the halogen is a Cl or a F. Beside the halogenation, both the six-membered rings and the five-membered ring may carry other substitutions such as, but not limited to, a methyl group or a O-methyl group. The heterocyclic five membered ring may comprise more than one non-carbon atom. Preferably, said non-carbon ring atoms are selected from the group consisting of O, N and S. Both individual ring structures do not share any C atom. Said ring structures may be connected directly by a carbon-carbon link, or indirectly by a hinge chain. Said hinge chain may comprise non carbon atoms and side chains. Preferably, said hinge chain is limited to maximum 5 atoms (with exclusion of the side possible chain), and preferably said non-carbon atoms are selected from the group consisting of O, N and S. Preferably, the side chain is a keton group or a methyl group. Promotion of lateral root growth, as used throughout the invention is measured by evaluating the number of lateral roots/cm root, as exemplified in the examples. Preferably, the use of a chemical compound according to the invention is the use of a compound selected from the group consisting of N-(5-chloro-2,4-dimethoxyphenyl)-2-phenoxypropanamide, ethyl 2-{[(4-chloro-2-methylphenoxy)acetyl]amino}-5,5-dimethyl-4,7-dihydro-5H-thieno[2,3-c]pyran-3-carboxylate, 5-(2,3-dichlorobenzyl)-1,3-thiazol-2-amine, (2,3-dichlorobenzylidene)[4-(4-morpholinyl)phenyl]amine, 3-(3-nitrophenyl)-N-[3-(trifluoromethyl)phenyl]acrylamide, N'-(2,3-dichlorobenzylidene)-3,4-dihydroxybenzohydrazide, (2,3-dichlorobenzylidene)(2-methyl-3-nitrophenyl)amine, N'-(2,4-dichlorobenzylidene)-2-oxo-2-(1-pyrrolidinyl)acetohydrazide, 4-{2-[(2-methylphenoxy)acetyl]carbonohydrazonoyl}benzoic acid, 4-{3-[(2,3-dichlorobenzylidene)amino]imidazo[1,2-a]pyridin-2-yl}-2-methoxyphenol, 3-methyl-2-thioxo-5-({5-[3-(trifluoromethyl)phenyl]-2-furyl}methylene)-1,3-thiazolidin-4-one, 5-[3-(trifluoromethyl)phenyl]-2-furaldehyde thiosemicarbazone, N-(3-acetylphenyl)-4-chloro-3-(4-morpholinylsulfonyl)benzamide, 2-[(4-chlorophenyl)thio]-N-(2-methoxybenzyl)propanamide, 3-phenyl-1,3-thiazolidine-2-carboxylic acid, and N-2-adamantyl-3-(3-nitrophenyl)acrylamide, as represented in FIG. 1. A preferred embodiment is the use of a compound to promote lateral root growth in plants, whereby said compound has the structure

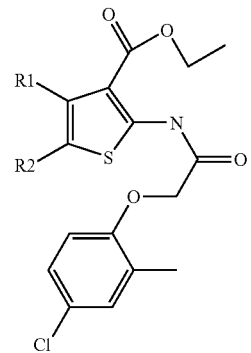

whereby R1 is methyl, ethyl, propyl, butyl or isobutyl and R2 is methyl or hydroxymethyl, or R1 and R2 form a closed ring with the structure —$CH_2$—C—$(CH_3)_2$—O—$CH_2$—.

A specially preferred embodiment is the use of a chemical compound to promote lateral root growth in plants, whereby said compound consists of the structure

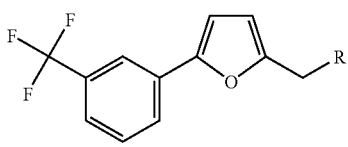

whereby R is any chemical structure. Preferably R is selected from the group consisting of =O, =N—N—C(=S)—N, and

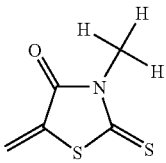

As a non limiting example, the heterocyclic ring may be further modified by linking a biotin group to the N position, using a cleavable linker.

Still another preferred embodiment is the use of a chemical compound to promote lateral root growth in plants, whereby said compound has the structure

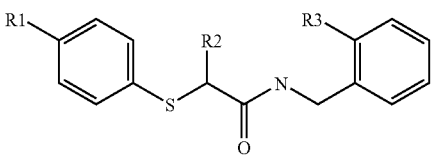

whereby R1 is H or a halogen, preferably Cl, R2 is H or a methyl group and R3 is H, methyl or OCH₃.

Another aspect of the invention is the use of a set of chemical compounds comprising at least an aromatic C six-membered ring and a C six-membered ring or a heterocyclic five-membered ring, whereby none of said C six-membered ring structures are linked in bicyclic structure, to derive lateral root growth promoting compounds in silico. Said structures don't comprise a naphthalene core nor an indole core; in case of a phenoxy core a second ring structure is present, distinguishing those compounds from the known auxin like compounds. The second C six-membered ring and the heterocyclic five-membered ring may be aromatic or not. Preferably the aromatic C six-membered ring is halogenated. Preferably, the halogen is a Cl or a F. Beside the halogenation both the six-membered rings and the five-membered ring may carry other substitutions such as, but not limited to a methyl group or a O-methyl group. The heterocyclic five membered ring may comprise more than one non-carbon atom. Preferably, said non-carbon ring atoms are selected from the group consisting of O, N and S. Both individual ring structures do not share any C atom. Said ring structures may be connected directly by a carbon-carbon link, or indirectly by a hinge chain. Said hinge chain may comprise non-carbon atoms and side chains. Preferably, said hinge chain is limited to maximum 5 atoms (with exclusion of the side possible chain), and preferably said non-carbon atoms are selected from the group consisting of O, N and S. Preferably, the side chain is a keton group or a methyl group. Indeed, on the base of structure, using charge, electrophilicity, lipophilicity, shape and softness as atomic properties, new compounds can be derived by the person skilled in the art that do have a similar functionality, but are not directly structural related. Examples of such compounds are given in the application.

Still another aspect of the invention is a method to promote lateral root growth in plants, comprising applying an effective amount of a chemical compound comprising at least an aromatic C six-membered ring and a C six-membered ring or a heterocyclic five-membered ring, whereby none of said C six-membered ring structures are linked in bicyclic structure. Said structure doesn't comprise a naphthalene core nor an indole core; in case of a phenoxy core a second ring structure is present, distinguishing those compounds from the known auxin-like compounds. The second C six-membered ring and the heterocyclic five-membered ring may be aromatic or not. Preferably the aromatic C six-membered ring is halogenated. Preferably, the halogen is a Cl or a F. Beside the halogenation, both the six-membered rings and the five-membered ring may carry other substitutions such as, but not limited to a methyl group or a O-methyl group. The heterocyclic five-membered ring may comprise more than one non-carbon atom. Preferably, said non-carbon ring atoms are selected from the group consisting of O, N and S. Both individual ring structures do not share any C atom. Said ring structures may be connected directly by a carbon-carbon link, or indirectly by a hinge chain. Said hinge chain may comprise non-carbon atoms and side chains. Preferably, said hinge chain is limited to maximum 5 atoms (with exclusion of the possible side chain), and preferably said non-carbon atoms are selected from the group consisting of O, N and S. Preferably, the side chain is a keton group or a methyl group. Said compound may be dissolved in a suitable solvent, preferable water, to form an aqueous solution that can be sprayed on the field.

EXAMPLES

Figure 1:
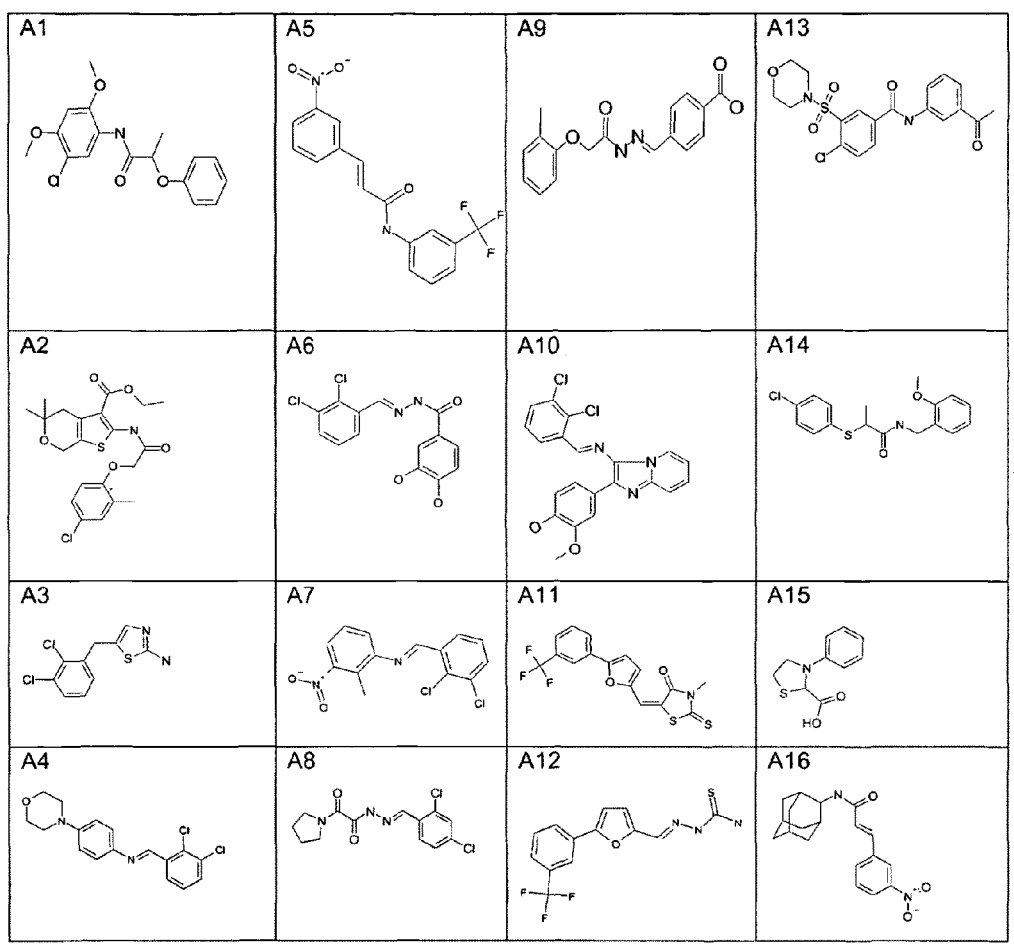
FIG. 1: Structures of the 16 selected activators of LR formation.

Materials and Methods to the Examples
Compound Screening Protocol

*Arabidopsis thaliana* (L.) Heynh. seeds were vernalised for 48 hours and three to four seeds were sown per well in 96-well filterplates (Multiscreen HTS MSBVS1210, Millipore, USA) in 75 µl liquid medium derived from standard Murashige and Skoog (MS) medium. Plates were put in a growth chamber under continuous light (110 µE.m$^2$.s$^1$ photosynthetically active radiation, supplied by cool-white fluorescent tungsten tubes; Osram) at 22° C. A commercial 10,000 compound library (DiverSet™, ChemBridge Corporation, USA) was used for screening. All compounds were dissolved in 100% DMSO at a stock concentration of 10 mM. Three days after germination (3DAG) the medium was removed on a vacuum manifold and 150 µl fresh medium was added to the plates to correct for evaporation. Compounds were added to this medium at a final concentration of 50 µM and plates were incubated for 24 hours. GUS-staining was performed overnight. All plates were screened visually (twice independently) for staining patterns using binocular microscopes (CETI, Belgium). Only wells with all plants giving the same pattern were selected for further analysis.

Dose-Response Analysis

For further phenotypic analysis, all plants were grown on vertically oriented square plates (Greiner Labortechnik, Austria) with solid medium derived from standard MS medium under the same conditions. 3 DAG plants were transferred to medium supplemented with compounds and were left to grow for another 7 days. After this, root length and number of LRs were counted using ImageJ 1.34 freeware.

Compounds and Derivatives

All hit compounds were purchased from ChemBridge Corporation, USA. The ID numbers are: A1 (ID:5627285); A2 (ID:5705560); A3 (ID:5753867); A4 (ID:5250185); A5 (ID:5263355); A6 (ID:5319448); A7 (ID:5375640); A8 (ID:5379395); A9 (ID:5467678); A10 (ID:5625917); A11 (ID:5853934); A12 (ID:5856819); A13 (ID:5919797); A14 (ID:6389571); A15 (ID:6142645) and A16 (ID:6519229). Derivatives A2var3 (ID:5799813), A2var5 (ID:5647091), A11var2 (ID:5889244), A14var1 (ID:5537855), A14var2 (ID:6390734), A14var5 (ID:6202090) were purchased from ChemBridge Corporation, USA. Derivatives A2var1 (ID:BAS00483417), A11var1 (ID:BAS00126433) and A14var4 (ID:BAS00850105) were purchased from Asinex, Russia. Derivative A11var3 (ID:526673) was purchased from Aldrich, USA. Derivative A11var4 (ID: 12810) was purchased from Fluka, Switzerland. Derivatives A2var4 (ID:STK024507) and A11var5 (ID:STK096837) were purchased from Vitas-M Laboratory, The Netherlands. NPA and NAA were purchased from Sigma, USA.

Quantitative Real-Time PCR

RNA was extracted with the RNeasy kit. Poly(dT) cDNA was prepared from 1 mg of total RNA with Superscript III reverse transcriptase (Invitrogen) and quantified on an Light-Cycler 480 apparatus (Roche) with the SYBR Green I Master kit (Roche) according to the manufacturers instructions. Target quantifications were performed with specific primer pairs designed with the Beacon Designer 4.0 (Premier Biosoft International). All PCRs were performed in triplicate. Expression levels were normalized to EEF1α4 and CDKA1;1 expression levels that did not show clear systematic changes in Ct value. The primers used to quantify gene expression levels were:

| Gene | forward primer 5'-3' | SEQ ID NO: | reverse primer 5'-3' | SEQ ID NO: |
|---|---|---|---|---|
| CDKA1;1 | ATTGCGTATTGCCACTCTCATAGG | 1 | TCCTGACAGGGATACCGAATGC | 2 |
| EEF1α4 | CTGGAGGTTTTGAGGCTGGTAT | 3 | CCAAGGGTGAAAGCAAGAAGA | 4 |
| CYP79B3 | AAAGTCATCTTCACGAAACAAGAA | 5 | TTTTAAGCATCGCCGGAAT | 6 |
| CYP79B2 | AAACTAAACTACGTCAAAGCTATCCTC | 7 | ACGTGGGGGAGGTTGAAG | 8 |
| TIR1 | CCTAAACTGCAGCGCCTCT | 9 | GGTTGAAGCAAGCACCTCA | 10 |
| ABP1 | TTGCATGGAATGAAAGAGGTT | 11 | TGTCTCTGAACCTGGAGCAA | 12 |
| ARF7 | AGAAAATCTTTCCTGCTCTGGAT | 13 | TGTCTGAAAGTCCATGTGTTGTC | 14 |
| IAA19 | GTGGTGACGCTGAGAAGGTT | 15 | CGTGGTCGAAGCTTCCTTAC | 16 |
| PIN1 | TACTCCGAGACCTTCCAACTACG | 17 | TCCACCGCCACCACTTCC | 18 |
| PIN3 | GAGGGAGAAGGAAGAAAGGGAAAC | 19 | CTTGGCTTGTAATGTTGGCATCAG | 20 |
| PIN4 | TTGTCTCTGATCAACCTCGAAA | 21 | ATCAAGACCGCCGATATCAT | 22 |
| LAX3 | TTACCTTTGCTCCTGCTCCTTC | 23 | ATCCATCCTCCTACCACTCTCG | 24 |
| AUX1 | AGTAGCAAATGACAACGGAACAG | 25 | AGAGCCACCGTGCCATAGG | 26 |
| PLT1 | ACGATATGCCTTCCAGTGATG | 27 | TTCAGACCCATTCCTTGTGC | 28 |
| CYCB1;1 | CCTGGTGGAGTGGTTGATTGATG | 29 | CGACATGAGAAGAGCACTGAGAC | 30 |
| CYCD3;1 | TTCGTTCGTAGACCACATTATCAGG | 31 | CGGAGATTACAGAGAGGAGGAGAC | 32 |

In Vitro Pull-Down Assays

Pull-down assays with wheatgerm-expressed TIR1-Myc were performed by combining 45 ml of IVTT reaction extract with 6.5 mg of biotinylated domain II peptide and 955 ml of EB containing 1 mg/ml BSA with auxin treatments as indicated. The assays were incubated for 30 min at 4° C. and recovered on streptavidin-agarose. The final processing of pull-down assays including electrophoresis, western transfer and blotting with anti-Myc antibodies has been described in Kepinski and Leyser, 2004.

In Silico Screening

A library of compounds against which to screen was assembled from compounds of almost 40 different vendors and comprised more than 7 million original compounds. A filtering and cleaning procedure was used to enhance the quality of the library and to guarantee that all compounds were 'lead-like'. Subsequently, a 3D-structure enumeration step was introduced to sample the conformational flexibility of the compounds, which resulted in a total of 11 million conformations. All conformations of the in-house database of compounds and the structures of the 88 activators of LR formation were converted to Spectrophores™ (Silicos, Belgium) using charge, electrophilicity, lipophilicity, shape and softness as atomic properties. Each property was converted to 12 Spectrophore™ points, which made that a complete Spectrophore™ for each conformation constituted 60 data points. The Spectrophores™ were computed with the default settings for accuracy and resolution. Spectrophore™ comparisons were performed by calculating the Euclidean distance between the corresponding Spectrophores™. Autophores were also generated from the 11 M conformations of the in-house database of vendor compounds and the 88 activators of LR formation. Autophores were computed with the default settings for accuracy and resolution, and were generated from four atomic properties: positive and negative electrostatic potentials, softness, and lipophilicities. A complete Autophore consisted of 160 data points for each molecular conformation. Autophore comparisons were performed by calculating the Euclidean distance between the corresponding data points.

Mutants

Afb1, Afb2, Afb3 and the triple mutant Tir1afb2afb3 were described by Dharmasiri et al. (2005). Tir1 was described by Ruegger et al., (1998); 1aa28 by Rogg et al., (2001); Tir7-1 by Ruegger et al., (1997); the Cyp79b2b3 double mutant by Ljung et al. (2005); the arf7arf19 double mutant by Fukaki et al., (2005); Aux1 by Bennett et al., (1996); Xbat32 by Nodzon et al., (2004), Axr1-12 by Timpte et al., (1995), Slr1 by Fukaki et al., 2002 and Axr3-1 by Collet et al., (2000) and the mutants were obtained from the publishing authors.

Example 1

Selection of Compounds with Lateral Root Growth Promoting Activity

A commercial 10,000 compound library (DIVERSet™, ChemBridge Corporation) was screened to identify small molecules that activate LR formation. Because induction of CYCB1;1 expression in the primary root of *Arabidopsis thaliana* is associated with LR formation, a LR inducible system was developed as a reporter assay for LR formation (Himanen et al., 2002). In this assay, transgenic *Arabidopsis thaliana* seeds (CYCB1;1::GUS) were germinated in 96-well plates in liquid MS-medium containing the auxin transport inhibitor N-1-naphthylphthalamic acid (NPA). Because auxin transport is required for LR initiation (Casimiro et al., 2001), NPA causes an arrest in LR formation and seedlings develop solely a primary root. After 72 hrs of germination, seedlings were incubated in library compounds (50 µM) for 24 hrs. Activators of LR formation induced CYCB1;1 expression in the primary root, which was easily detected using a stereomicroscope. After analysis of the complete library, 99 compounds were identified that induced CYCB1;1 expression in the primary root. In a confirmation screen, the CYCB1;1 inducing effect in the primary root was confirmed for 88 compounds, while 66 of these activators still exerted their effect at 25 µM. Based upon potency and structural dissimilarity to the known activators of LR development i.e. auxin (indole-3-acetic acid, IAA), 1-naphthylacetic acid (NAA), 2,4-dichlorophenoxyacetic acid (2,4-D) and sirtinol, 16 activators (FIG. 1) were selected for further follow-up.

Example 2

Most of the Lateral Root Growth Promoting Compounds do not Bind to the Auxin Receptor TIR1

Figure 2:
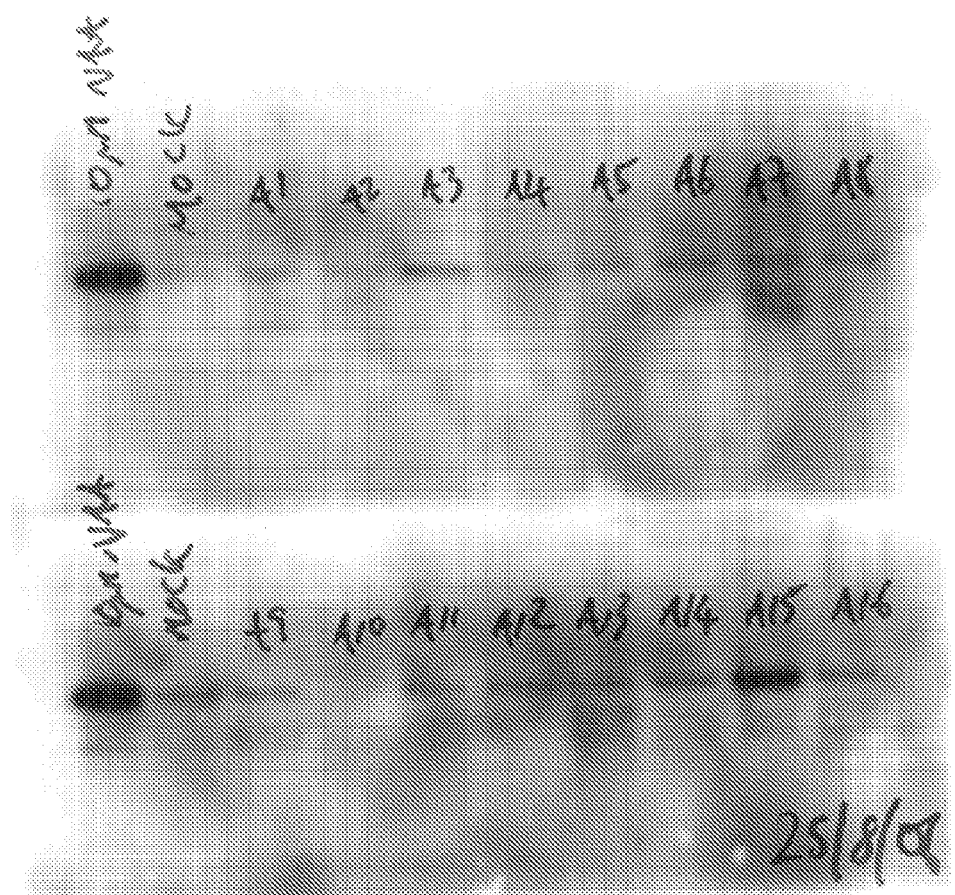
FIG. 2: In vitro binding assay to analyze binding of the 16 selected activators to the auxin receptor TIR1.

Earlier studies have shown that sirtinol is metabolized in vivo to NAA (Dai et al., 2005) while IAA, NAA, 2,4-D act by binding directly to the auxin-receptor TIR1 (Kepinski and Leyser, 2005). To demonstrate that the selected activators did not require TIR1 binding to exert their effect, binding to TIR1 was assessed in an in vitro binding assay (FIG. 2). Indeed, although activator A15 and to a lesser extent A3 could bind to TIR1, the other selected activators were as such not capable of TIR1 binding. These results indicate that with the exception of A3 and A15, the selected activators act differently compared to auxin, although it cannot be excluded that for some of the activators prior metabolization events in planta are required to bind to TIR1.

Example 3

Dose Response Curves of the Lateral Root Growth Promoting Compounds

Figure 3:
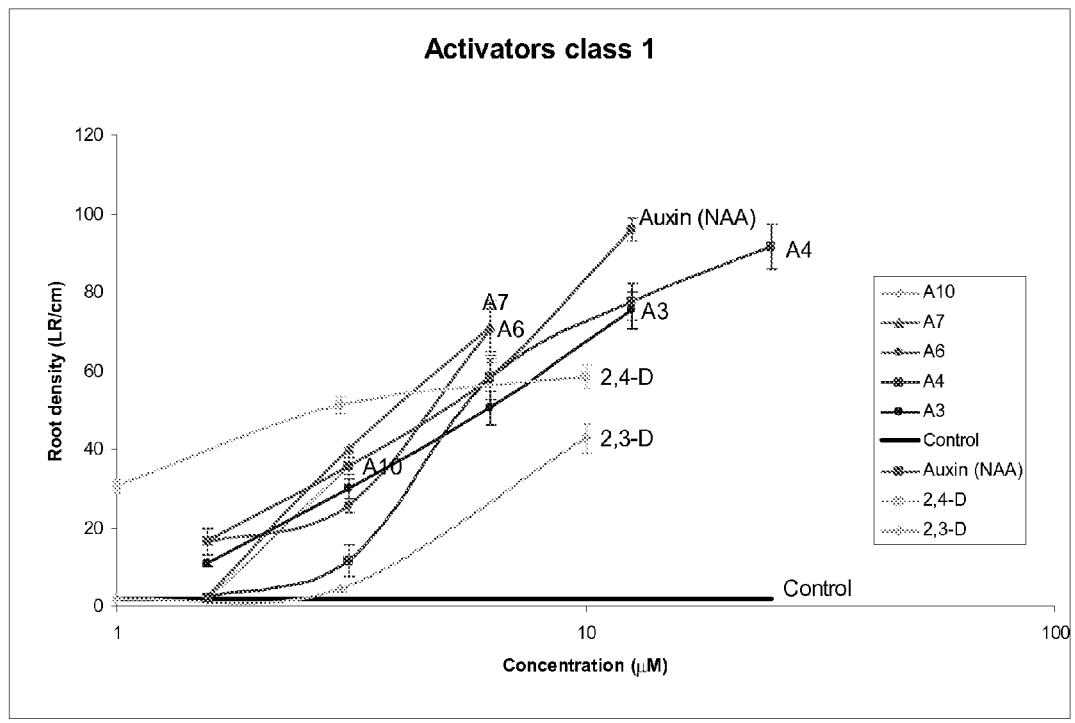
FIG. 3: Dose-response analysis of class 1 (upper panel) and class 2 (lower panel) activators. Wild-type *Arabidopsis thaliana* seeds were germinated under standard conditions on agar plates. After 3 days of germination, seedlings were transferred to agar plates containing compound at different concentrations. Lateral root density was measured 10 days after germination. Bars represent standard errors.
Figure 3:
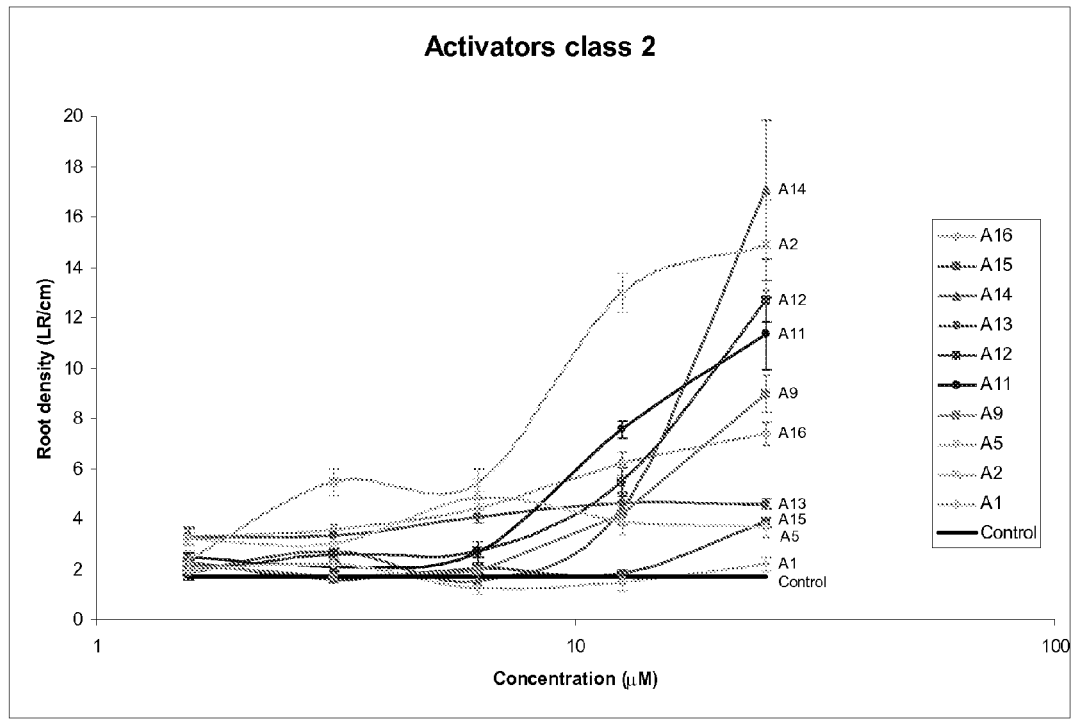

As a subsequent step, the phenotypic effect of the 16 selected activators was determined in a dose-response analysis in which LR density (number of LRs per cm) was quantified (FIG. 3). Based upon potency and structure, two different classes of activators could be identified. Class 1 compounds contained the highly potent activators of LR development with a potency level similar to that of the synthetic auxin NAA. Interestingly, these activators shared a common substructure (2,3-dichlorobenzaldehyde, 2,3-D) that was important in the LR-inducing effect. Class 2 activators were less potent but contained compounds with unique structures. The most potent activators of class 2 (compounds A2, A11, A12, A14) were selected for further detailed characterization. Interestingly, activators A11 and A12 shared a large common substructure (5-[3-(trifluoromethyl)phenyl] furan-2-carbaldehyde), which could imply that they act by interacting with the same target protein(s).

Figure 4:
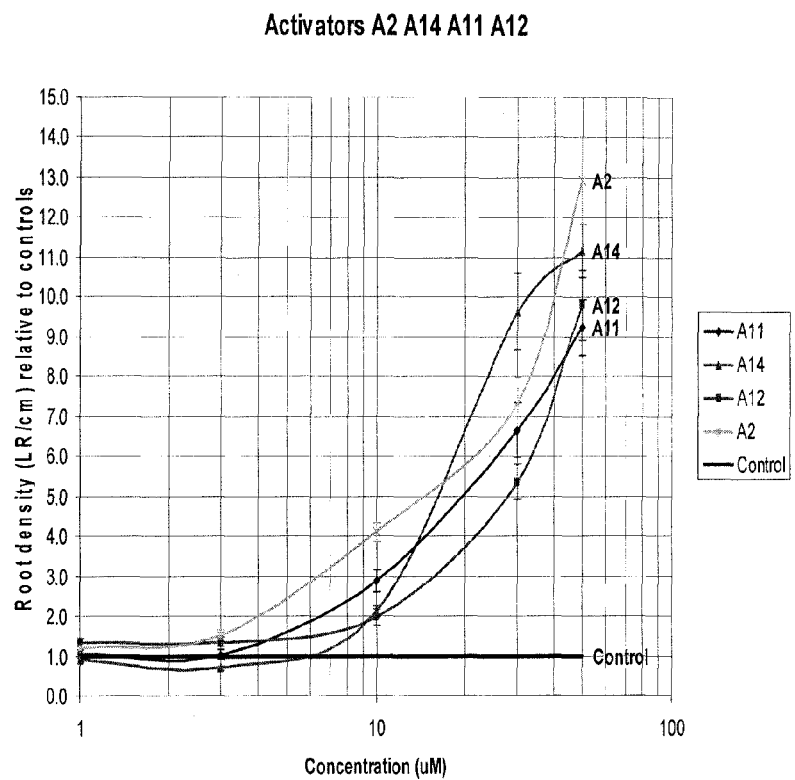
FIG. 4: Dose-response analysis of A2, A11, A12, A14 and NAA. Wild-type *Arabidopsis thaliana* seeds were germinated under standard conditions on agar plates. After 3 days of germination, seedlings were transferred to agar plates containing compound at different concentrations and 1% DMSO. Plants transferred to agar plates containing 1% DMSO and no compound were used as controls. Lateral root density (left panels) and root length (right panels) were measured 10 days after germination. Bars represent standard errors.
Figure 4:
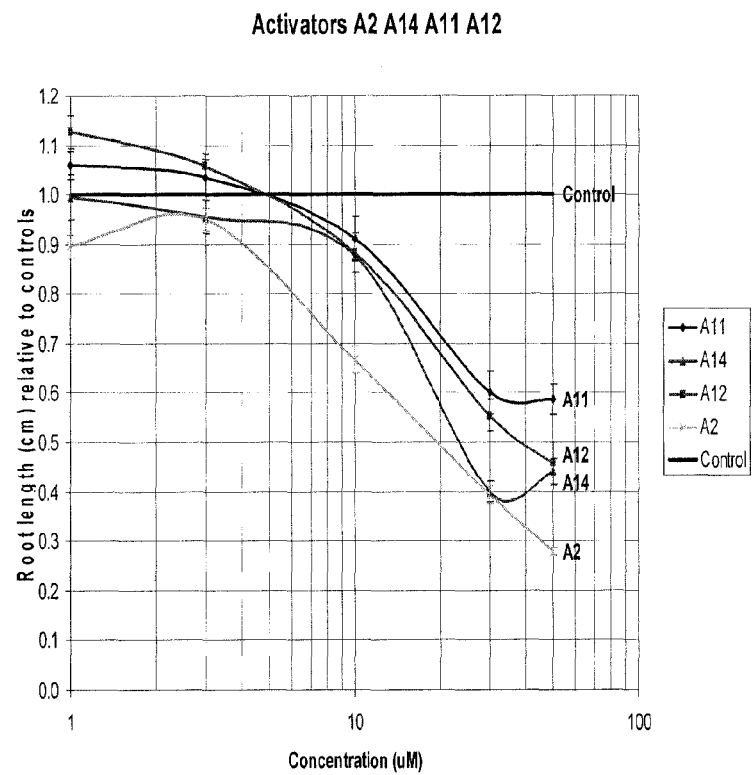
Figure 4:
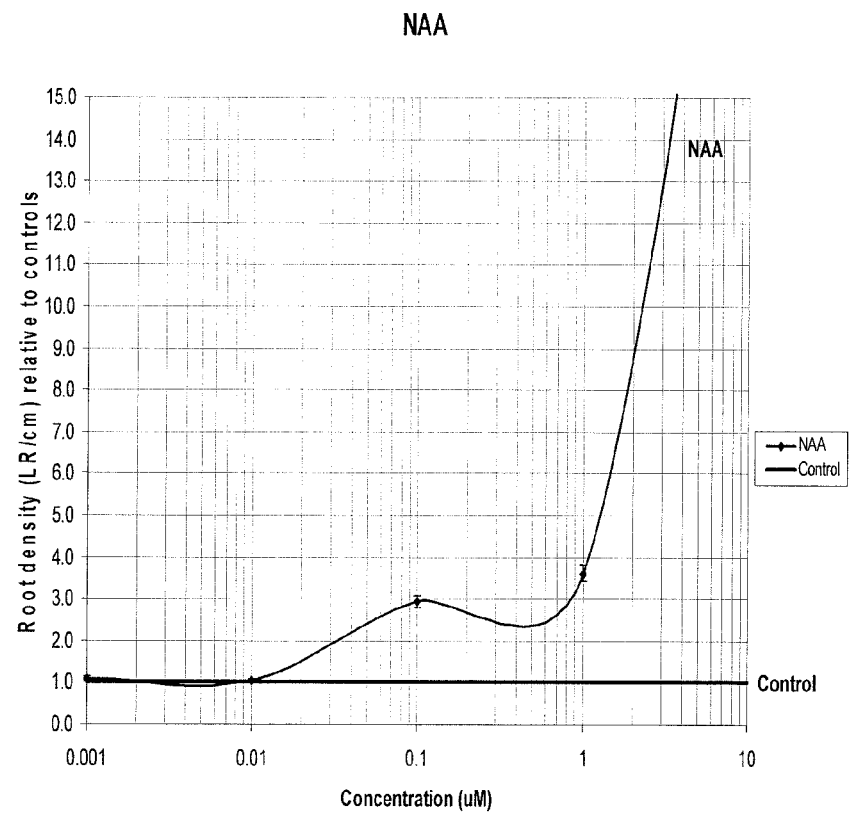
Figure 4:
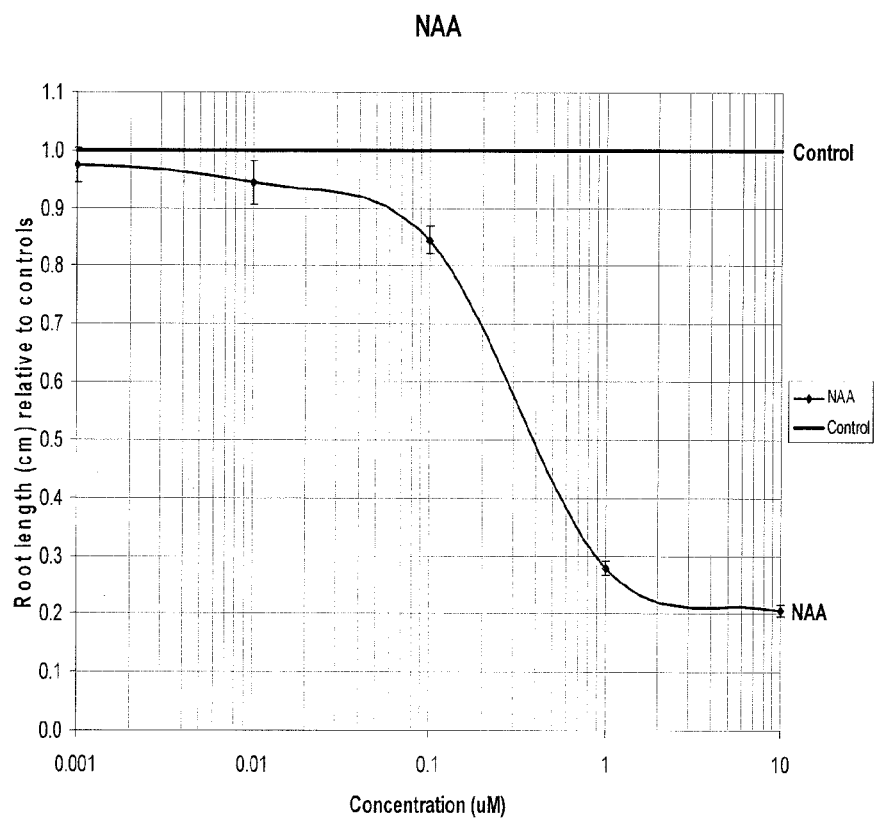

The phenotypic effect of the activators A2, A11, A12 and A14 on root development was compared with the auxin analogue NAA (FIG. 4). At a given increase in root density, the selected activators had a less negative effect on root elongation compared to NAA. If a compound concentration was applied that increased root density five times compared to controls (20 µM for A11 and 1.5 µM for NAA), than the root length in the presence of NAA was reduced drastically (0.2 times the root length of controls) while the root length was less affected with A11 (0.7 times the root length of controls). This observation could imply that the selected activators act more specifically on LR initiation without having an effect on other processes compared to NAA. Furthermore, increasing the compound concentration of the selected activators resulted in a gentle increase in LR density, while NAA worked with a threshold-like mechanism and had an 'all-or-nothing' effect. Consequently, the activators are more tunable than NAA to induce LR formation.

Example 4

Analysis of Gene Expression Induced by Lateral Root Growth Promoting Compounds

Figure 5:
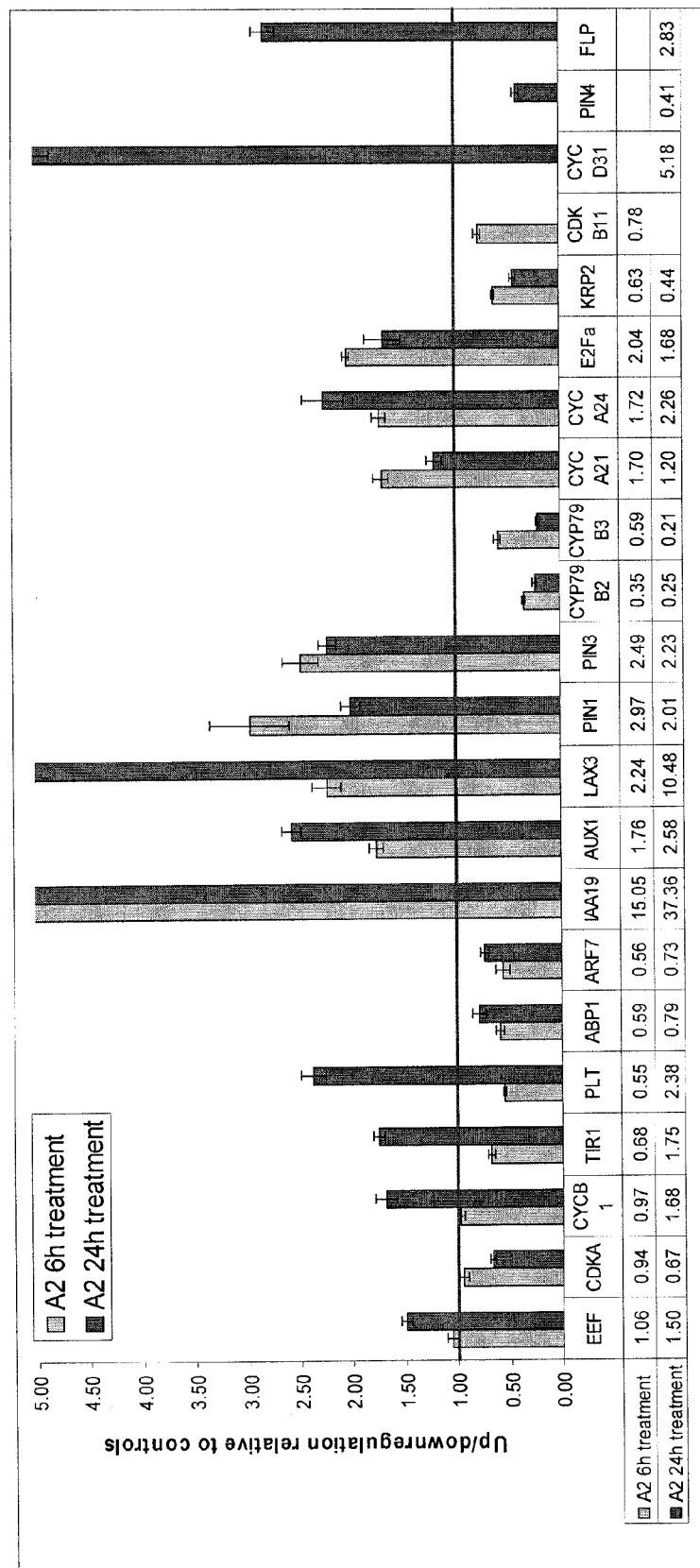
FIG. 5: Transcript profiling of roots of wild-type *Arabidopsis thaliana* plants after 6 hrs or 24 hrs treatment with A2 (upper panel), A14 (middle panel) or A11 (lower panel) at a concentration of 30 μM.
Figure 5:
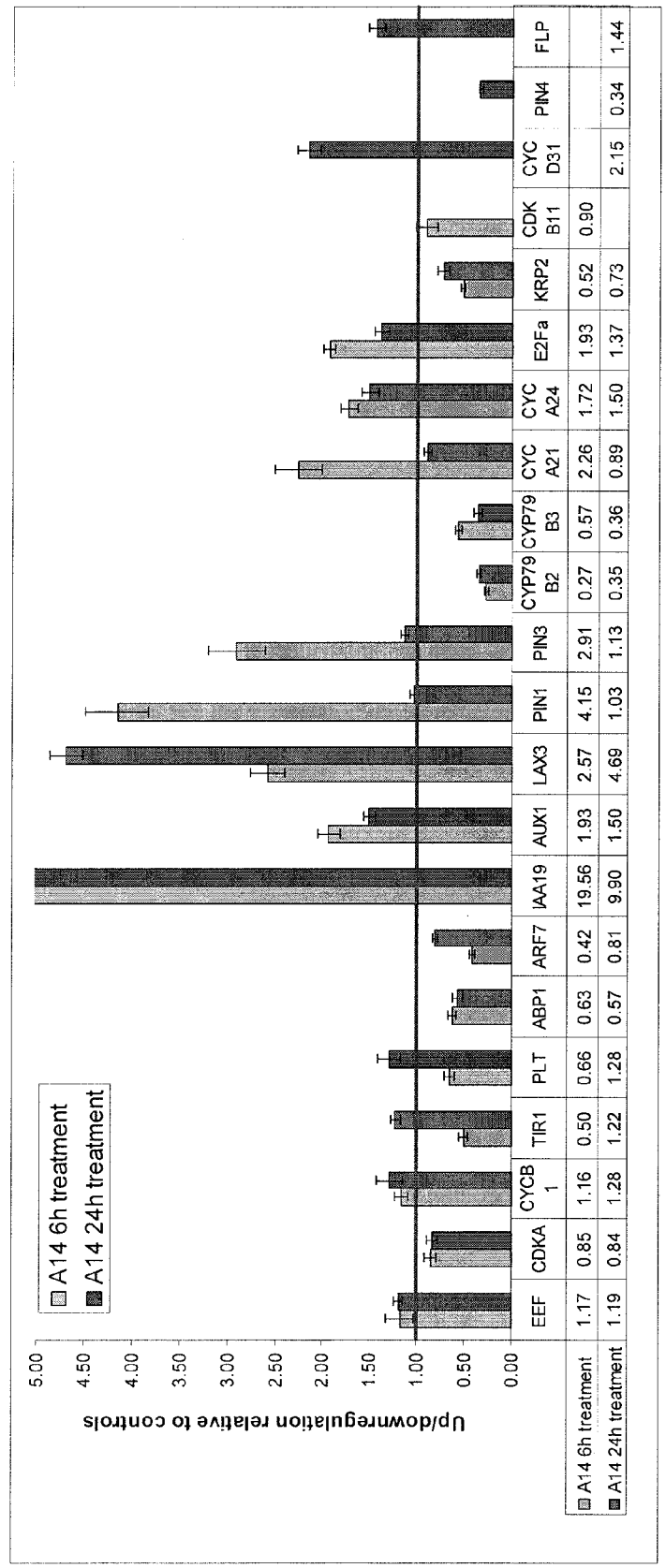
Figure 5:
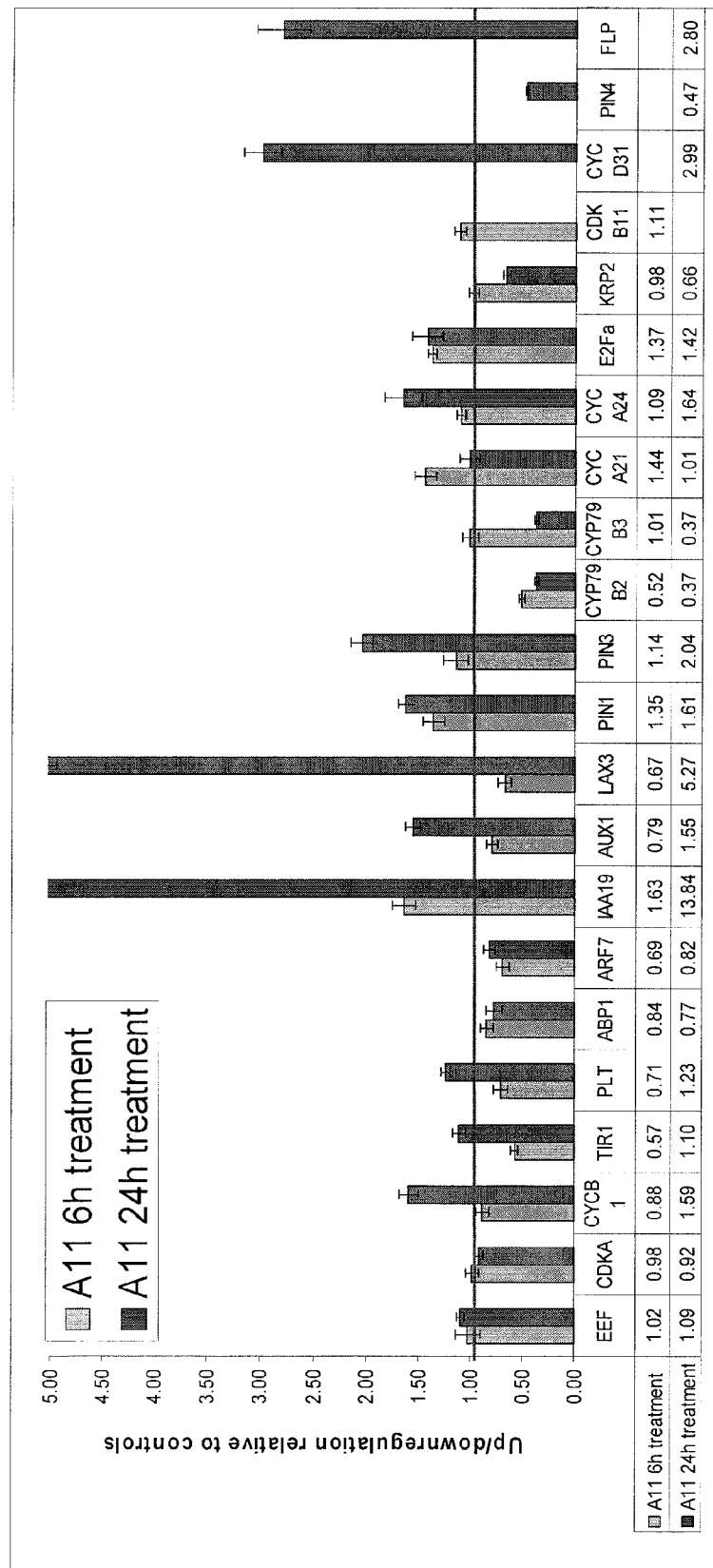

Using Q-PCR, the expression of selected genes involved in auxin biosynthesis, auxin transport, auxin signaling and cell cycle was analyzed in response to compound treatment (FIG. 5). The results showed that A2 and A14 already exert their effect in the early stages of LR initiation (6 h) and have a similar expression pattern for the selected genes. A11 acts in late stages of LR initiation (24 h) and probably has a different mechanism of action than A2 and A14.

Example 5

Identification and Analysis of Structural Variants

Figure 6:
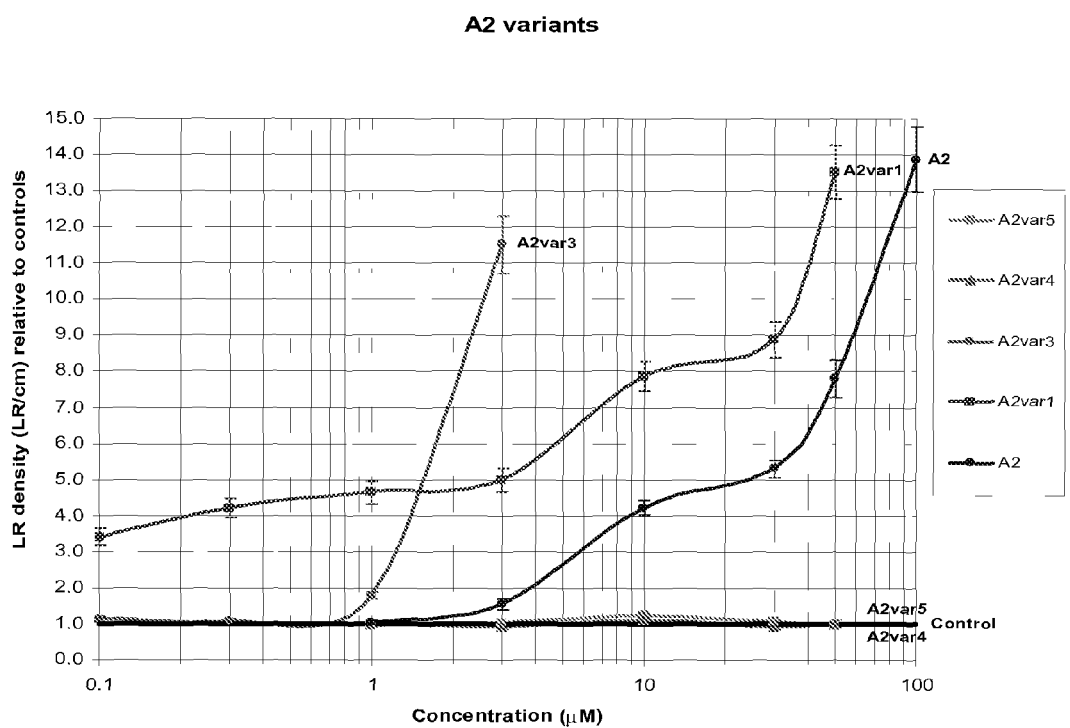
FIG. 6: Structure-activity analysis of A2. Upper panel: relative lateral root density. Lower panel: relative root length. The structure of the variants is given in FIG. 10.
Figure 6:
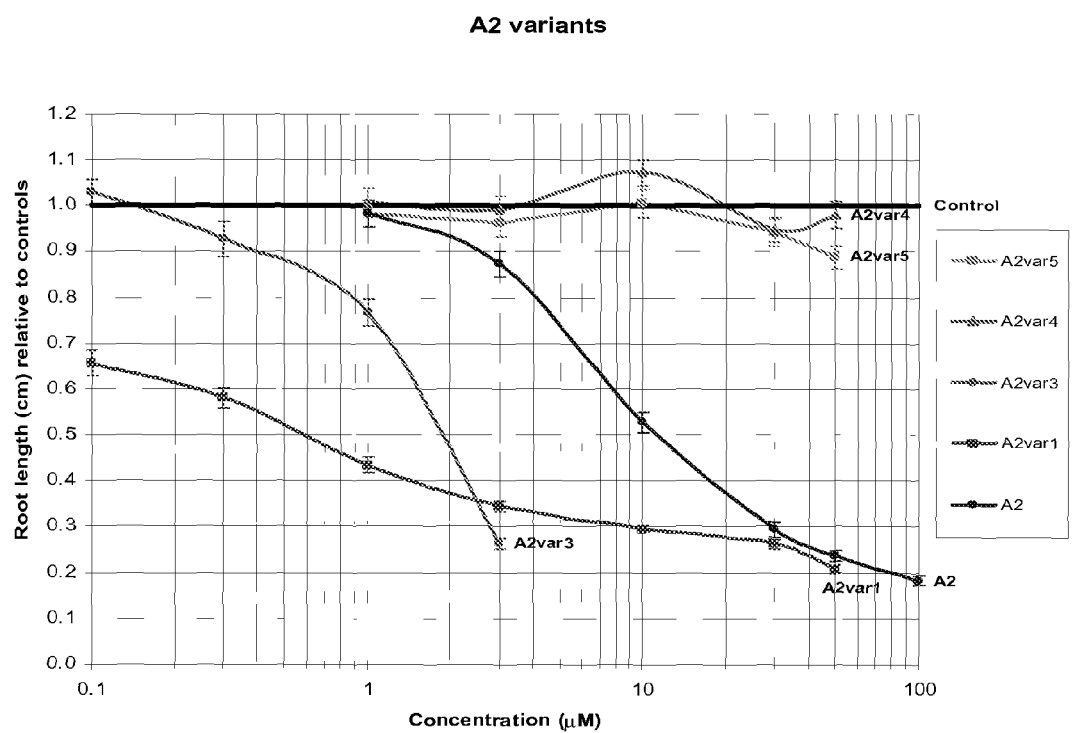
Figure 7:
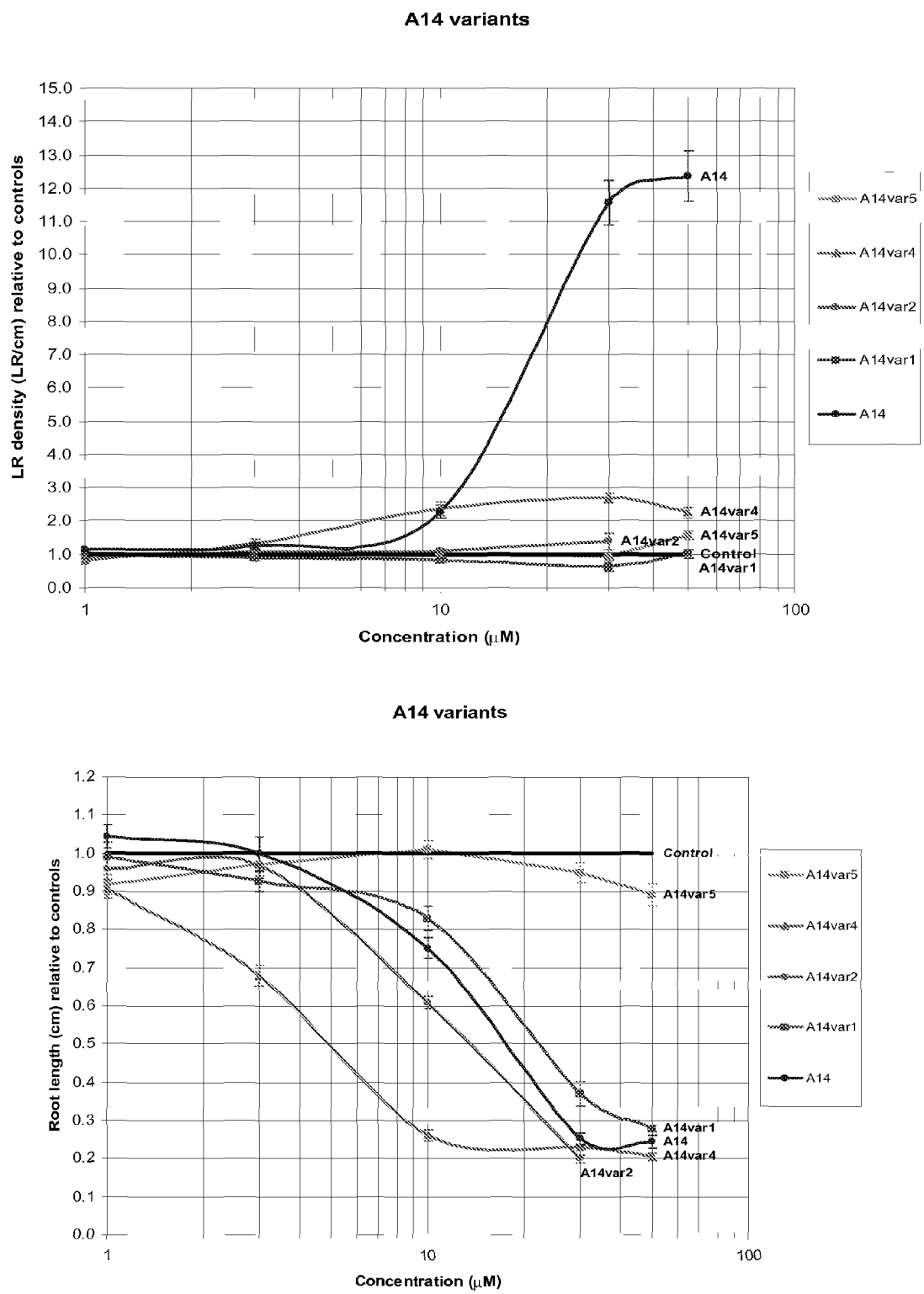
FIG. 7: Structure-activity analysis of A14. Upper panel: relative lateral root density. Lower panel: relative root length. The structure of the variants is given in FIG. 12.
Figure 8:
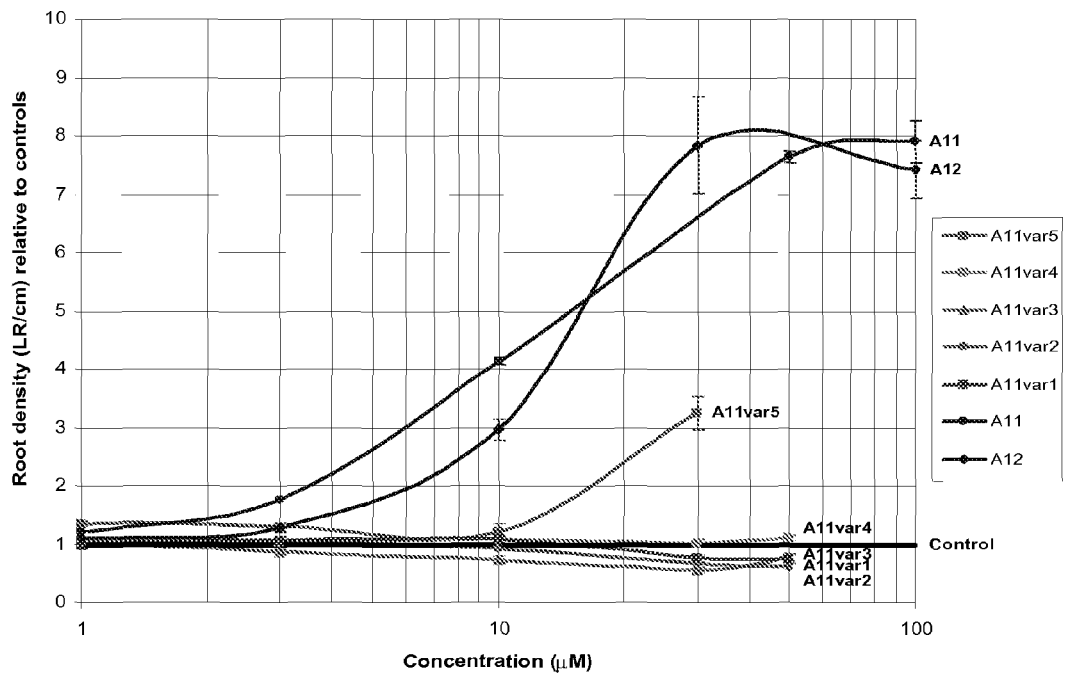
FIG. 8: Structure-activity analysis of A11. Upper panel: relative lateral root density. Lower panel: relative root length. The structure of the variants is given in FIG. 11.
Figure 8:
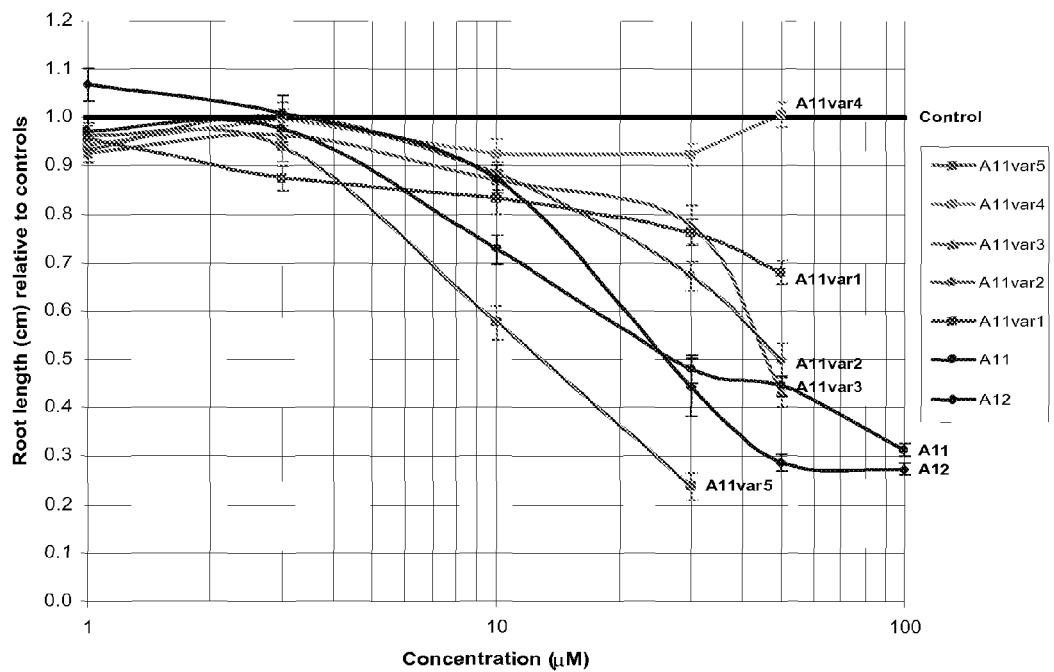

Several structural variants of A2 were analyzed for their effect on LR formation, as indicated by measuring LR density (FIG. 6). A2var3 was more potent compared to the original hit compound A2. At low concentrations (<1 µM), A2var1 was the most potent activator of LR formation, comparable to NAA and 2,4-D, however with less negative effects on primary root elongation. Structure-activity analysis of activator A14 demonstrated that all tested derivatives completely abolish the activity, indicating that every substructure or functional group of A14 is required to induce LR formation (FIG. 7). Analysis of the structural variants of activator A11 showed that A11var5 is the minimal substructure required to induce LR formation while R group substitutions at the aldehyde group have an effect on the potency of the compound (FIG. 8).

Example 6

In Silico Screening of Alternative Lateral Root Promoting Compounds

Figure 9:
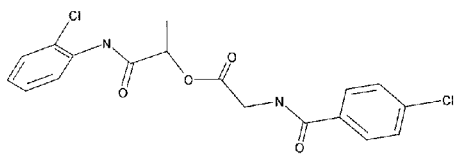
FIG. 9: Structures of the in silico derived compounds with a high similarity to the 88 initially identified activators.
Figure 9:
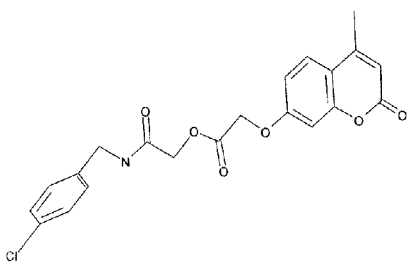
Figure 9:
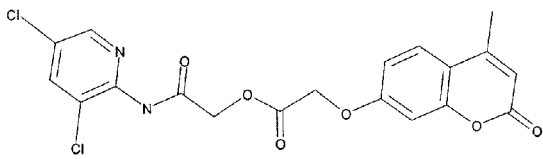
Figure 9:
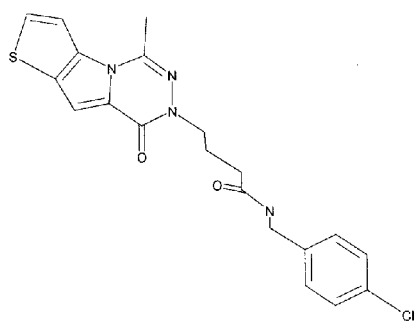
Figure 9:
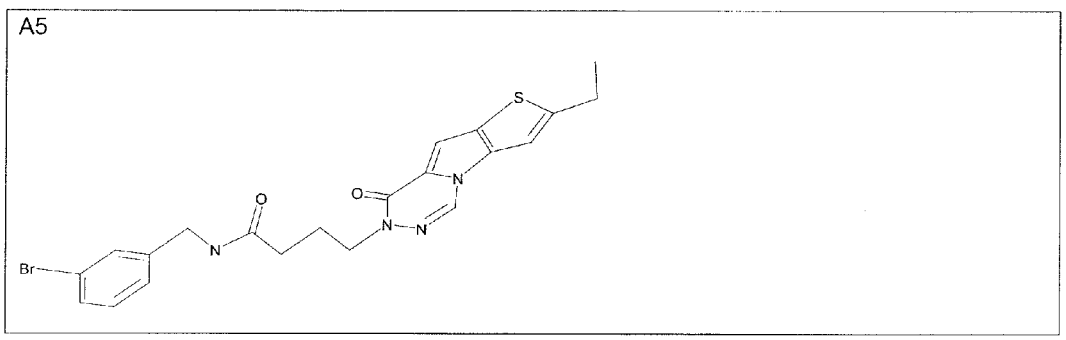
Figure 9:
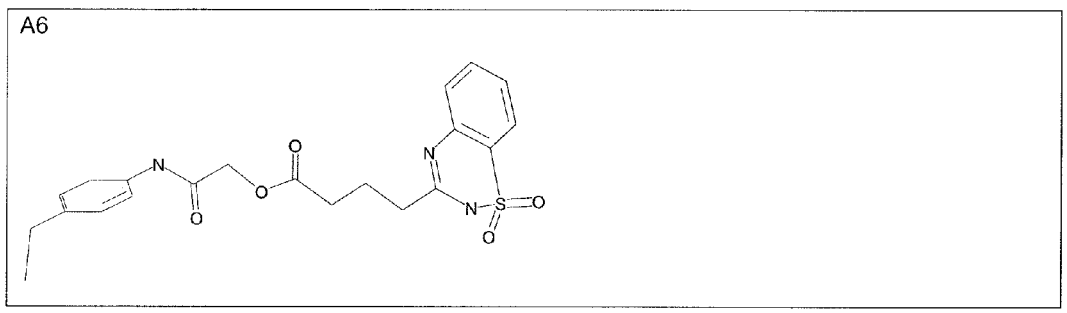
Figure 9:
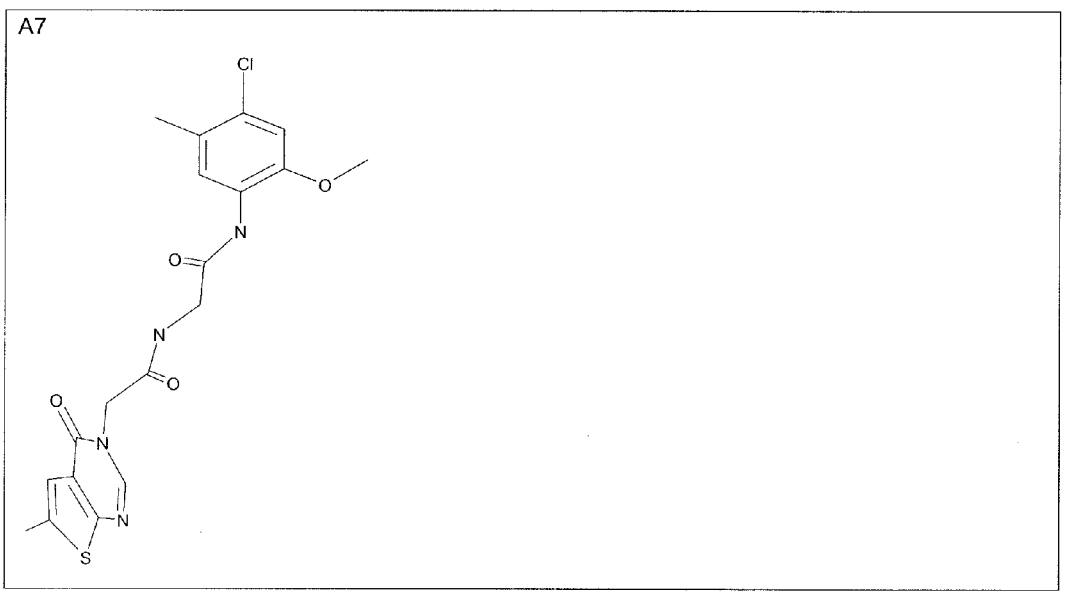
Figure 9:
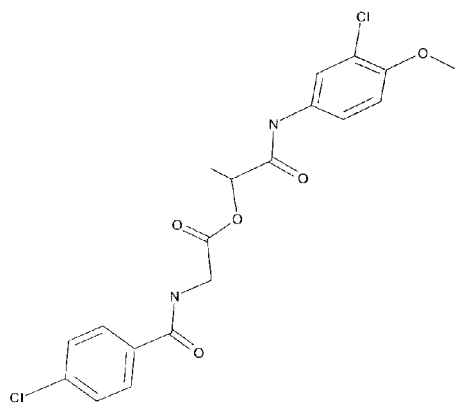
Figure 9:
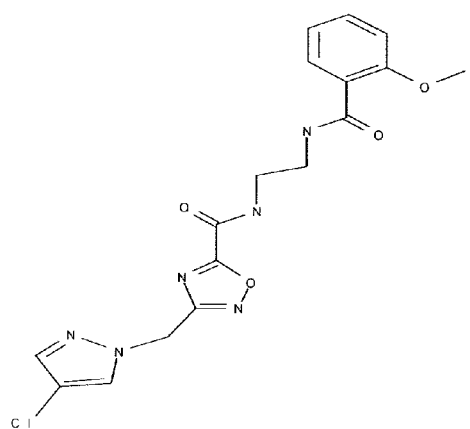
Figure 9:
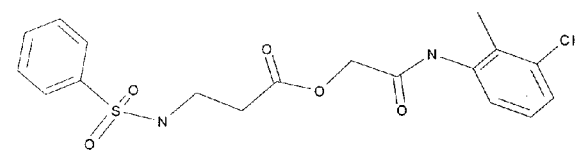
Figure 9:
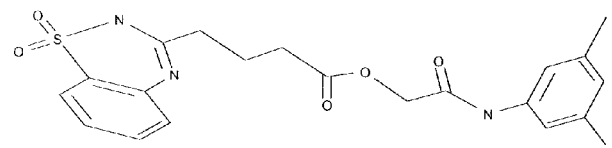
Figure 9:
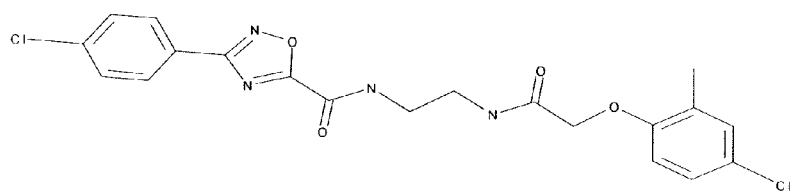
Figure 9:
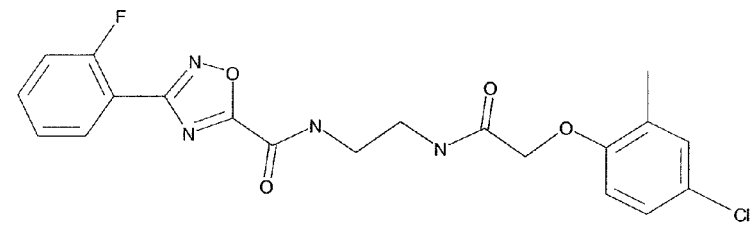
Figure 9:
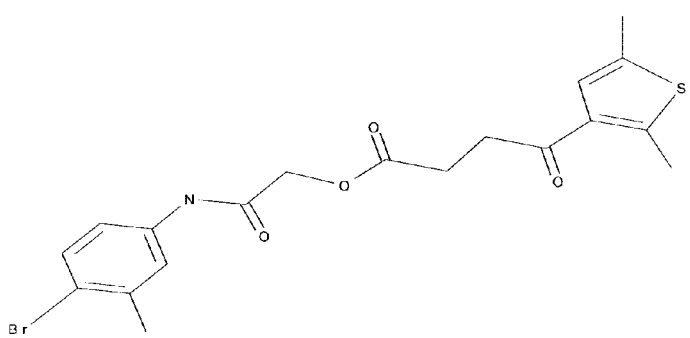
Figure 9:
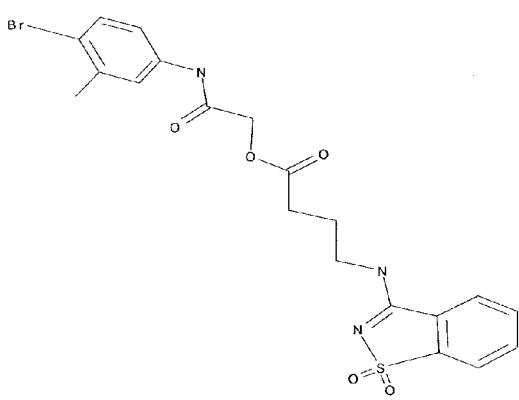
Figure 9:
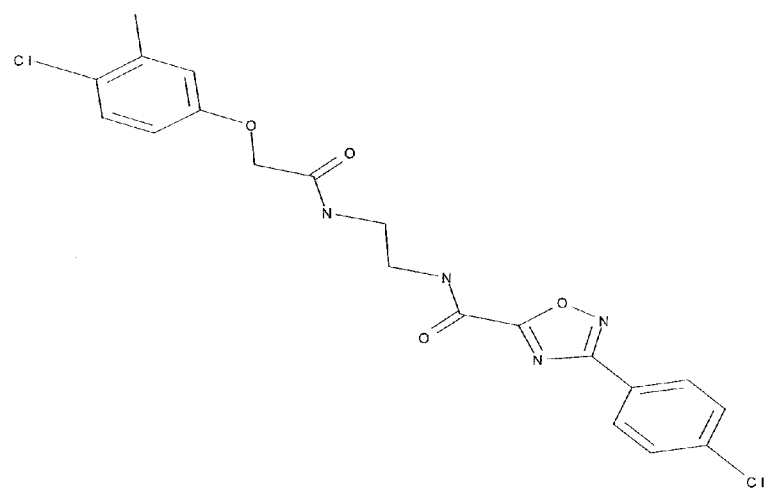
Figure 9:
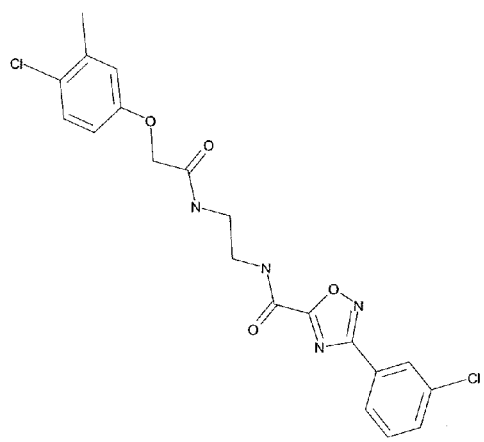
Figure 9:
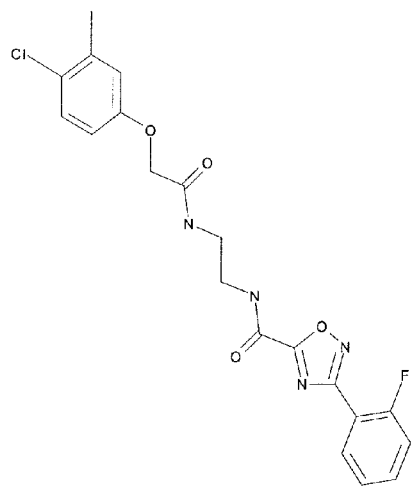
Figure 9:
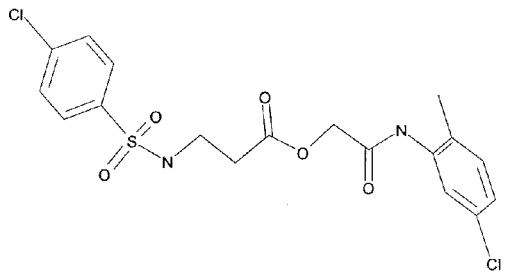
Figure 9:
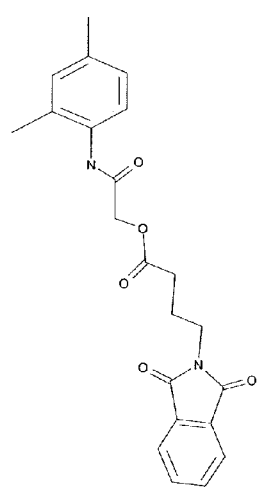
Figure 9:
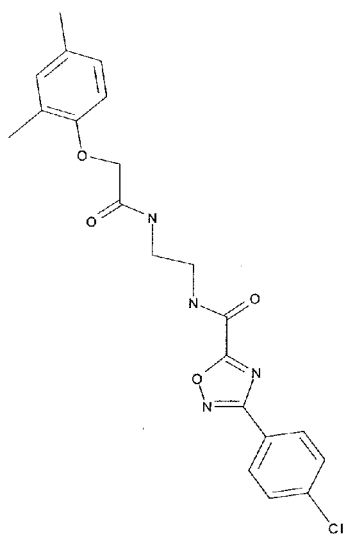
Figure 9:
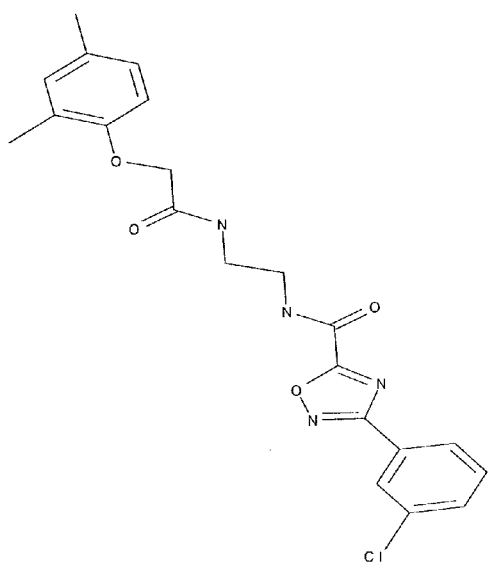
Figure 9:
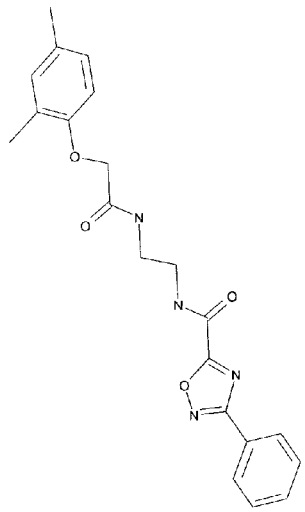
Figure 9:
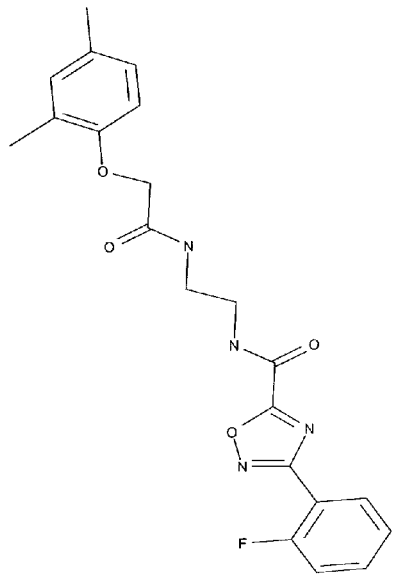
Figure 9:
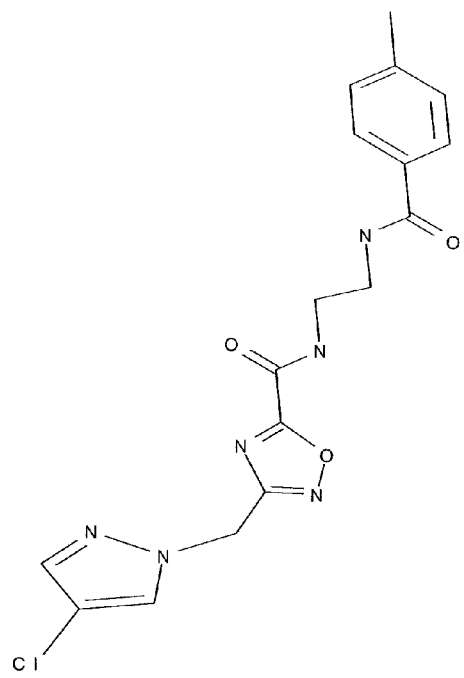
Figure 9:
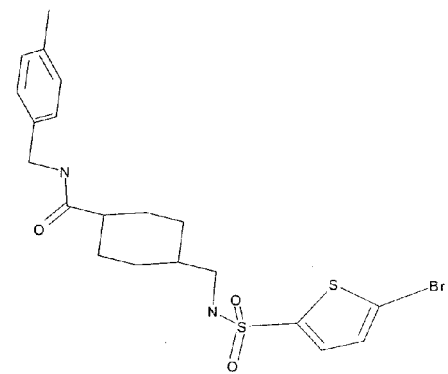
Figure 9:
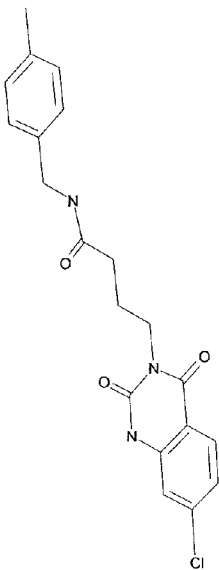
Figure 9:
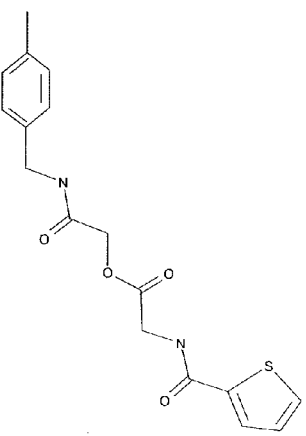
Figure 9:
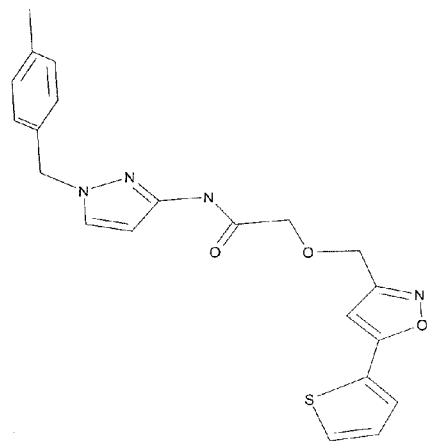
Figure 9:
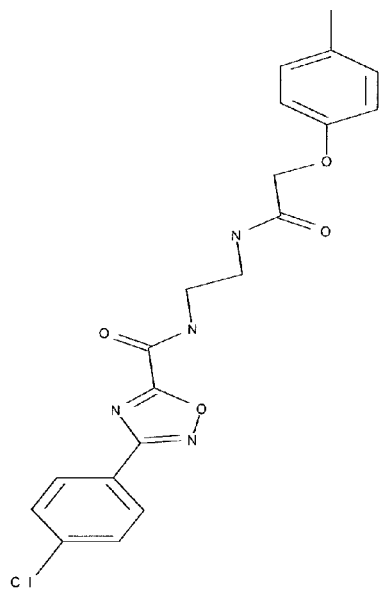
Figure 9:
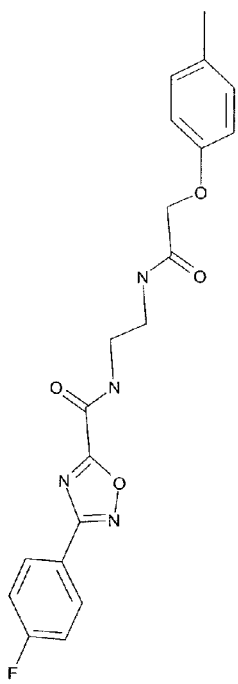
Figure 9:
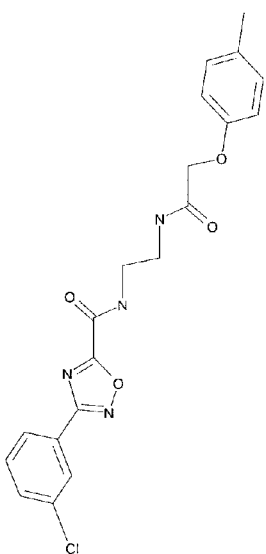
Figure 9:
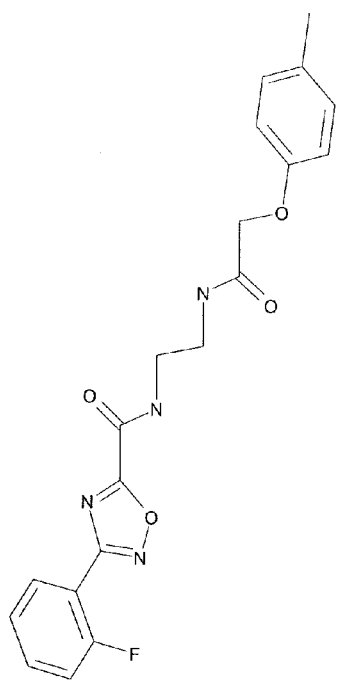
Figure 9:
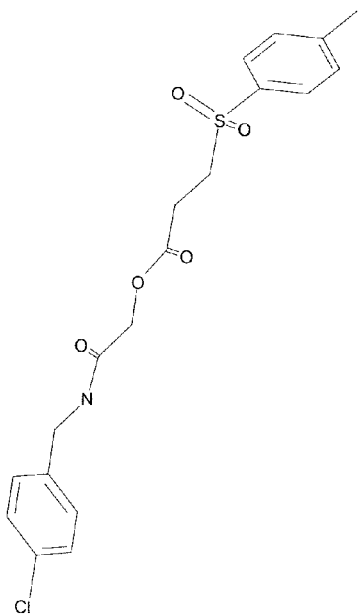
Figure 9:
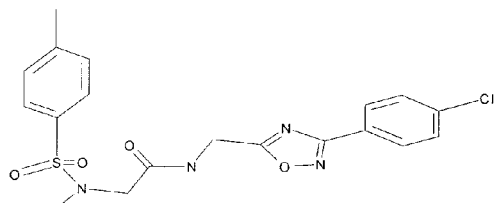
Figure 9:
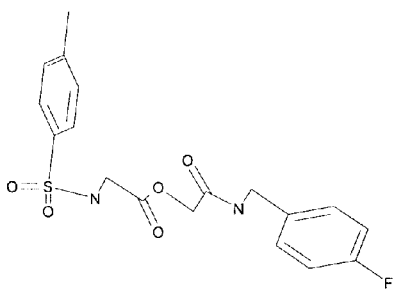
Figure 9:
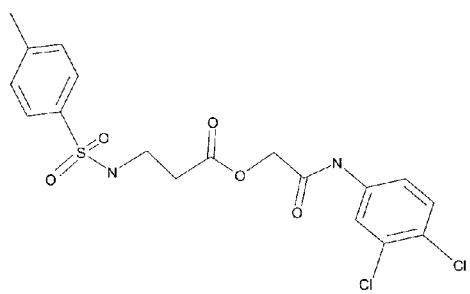
Figure 9:
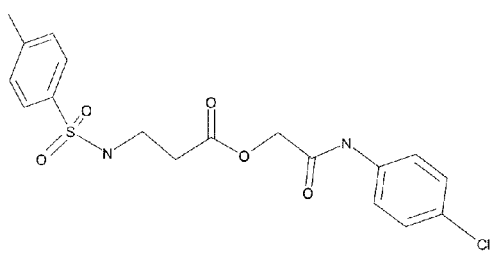
Figure 9:
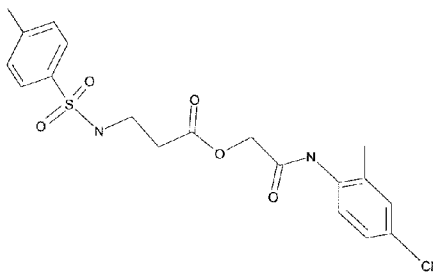
Figure 9:
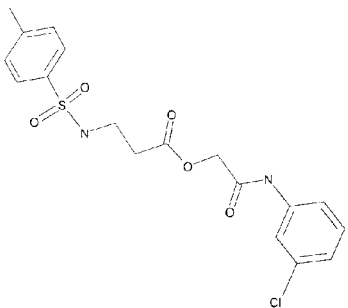
Figure 9:
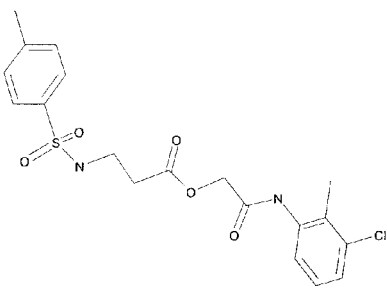
Figure 9:
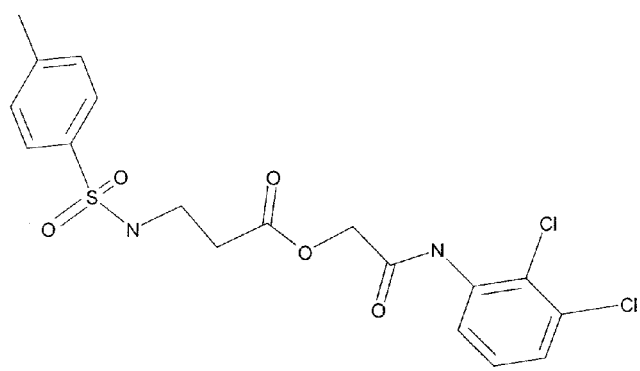
Figure 9:
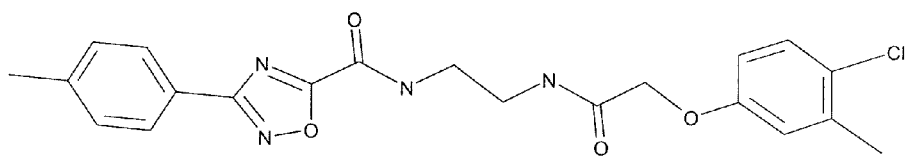
Figure 9:
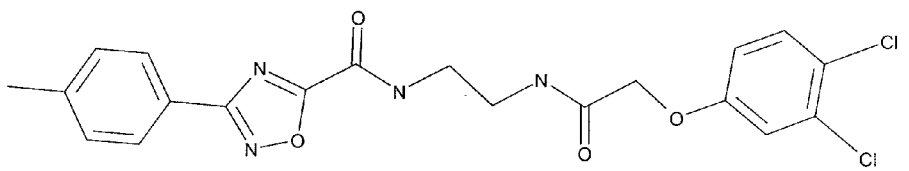
Figure 9:
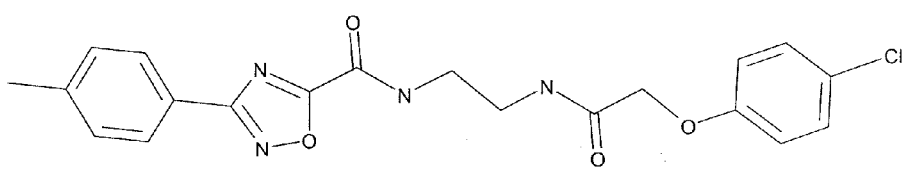
Figure 9:
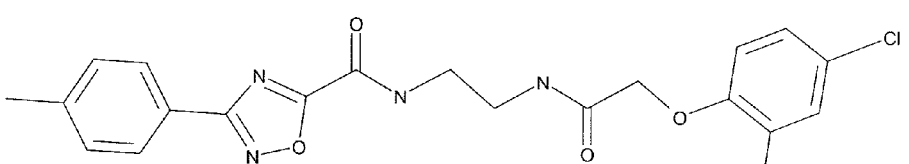
Figure 9:
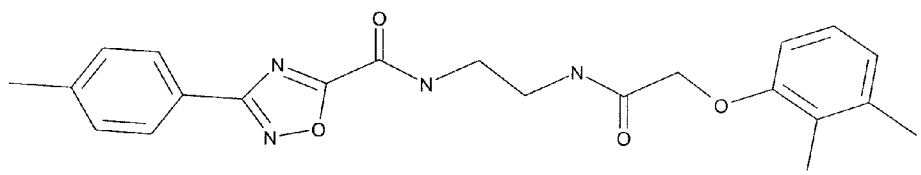
Figure 9:
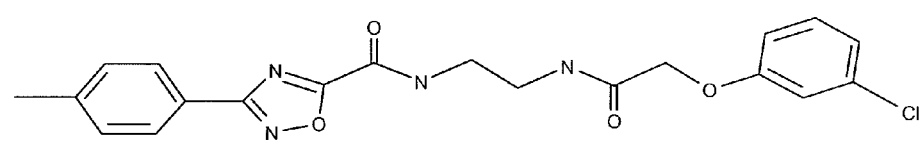
Figure 9:
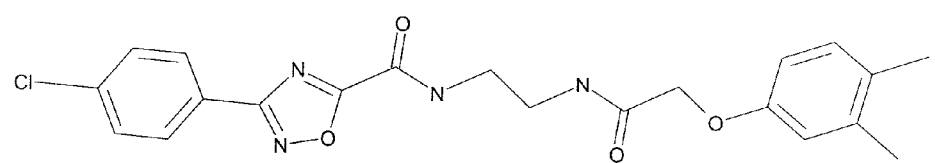
Figure 9:
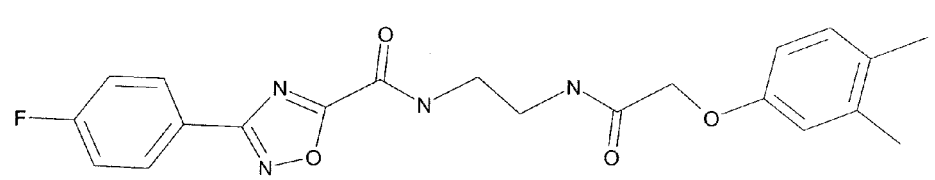
Figure 9:
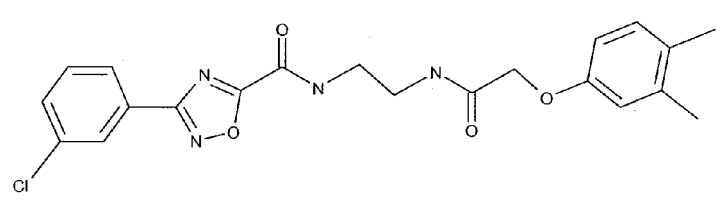
Figure 9:
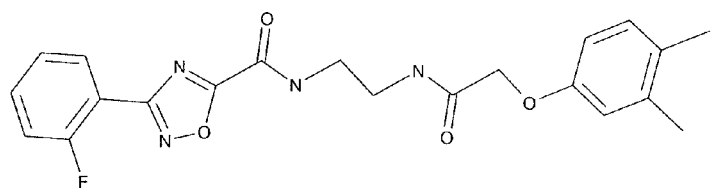
Figure 9:
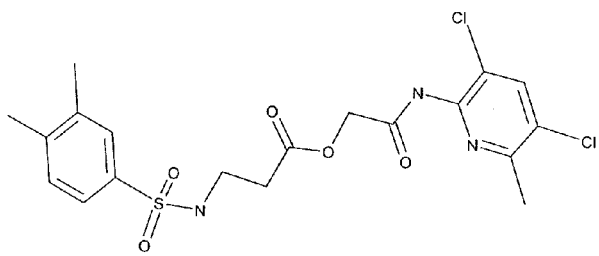
Figure 9:
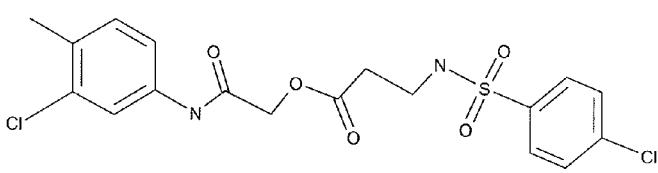
Figure 9:
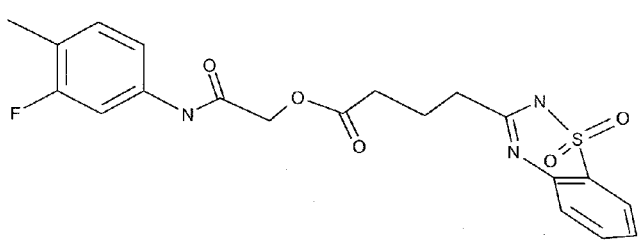
Figure 9:
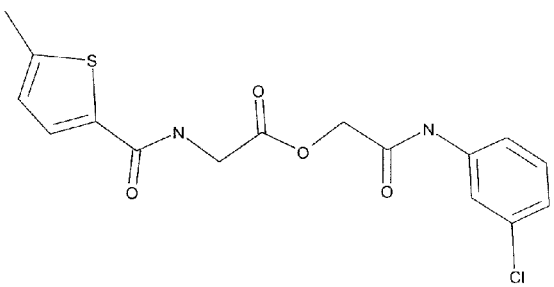
Figure 9:
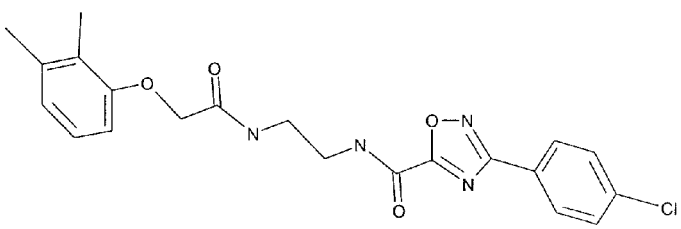
Figure 9:
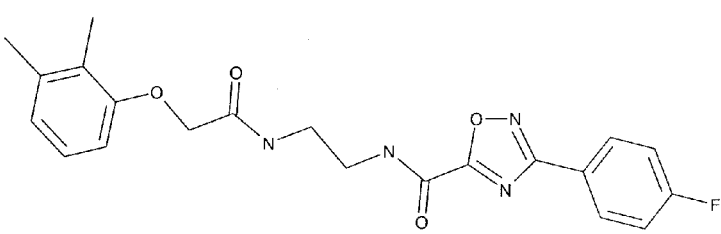
Figure 9:
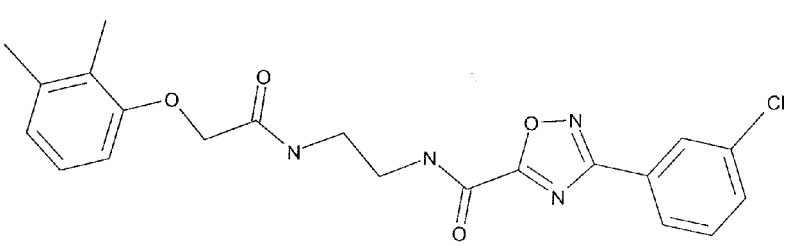
Figure 9:
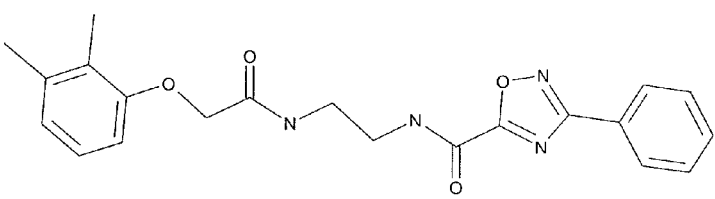
Figure 9:
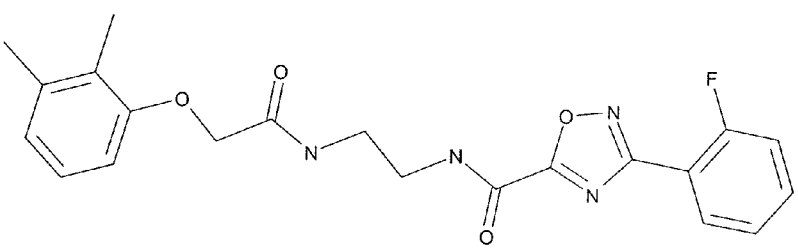
Figure 9:
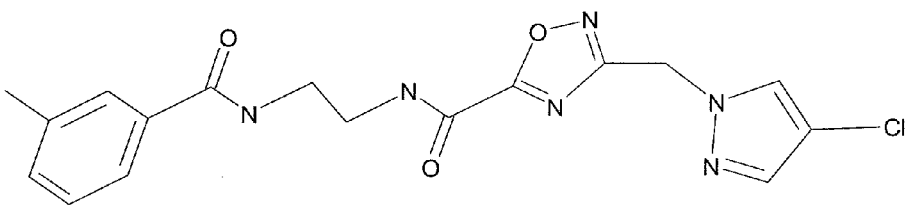
Figure 9:
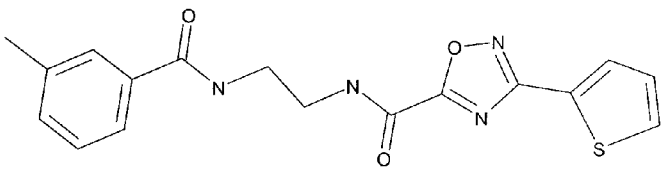
Figure 9:
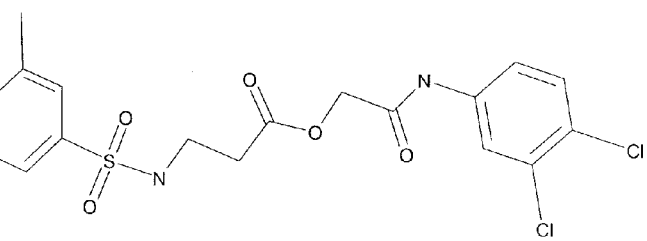
Figure 9:
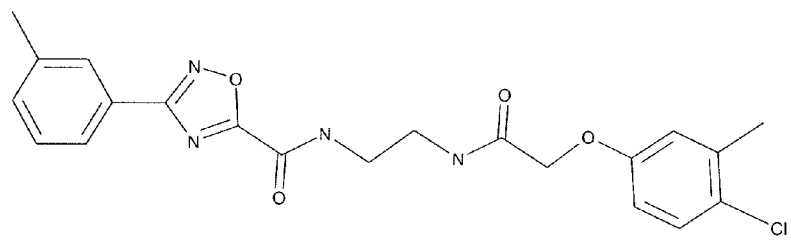
Figure 9:
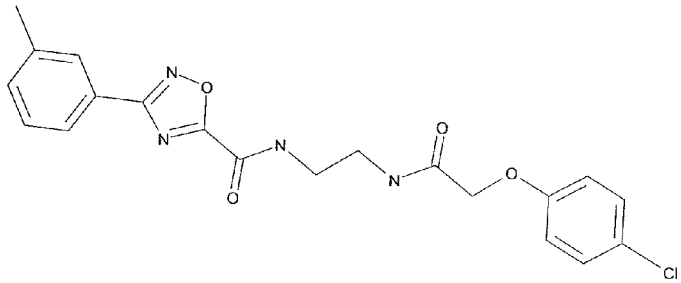
Figure 9:
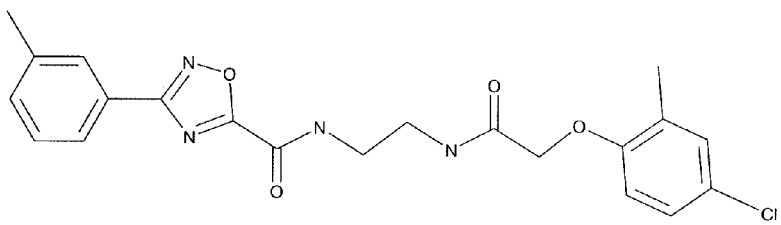
Figure 9:
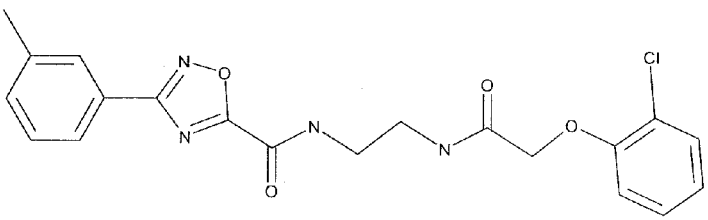
Figure 9:
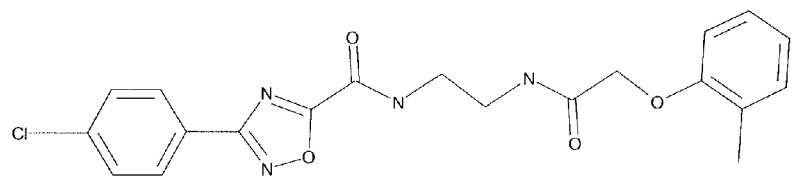
Figure 9:
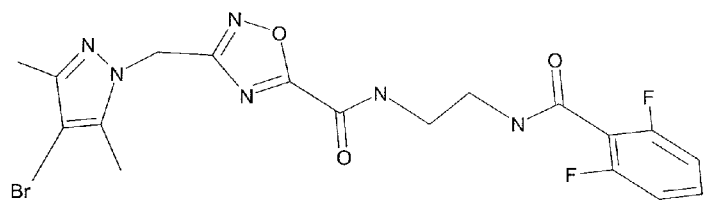
Figure 9:
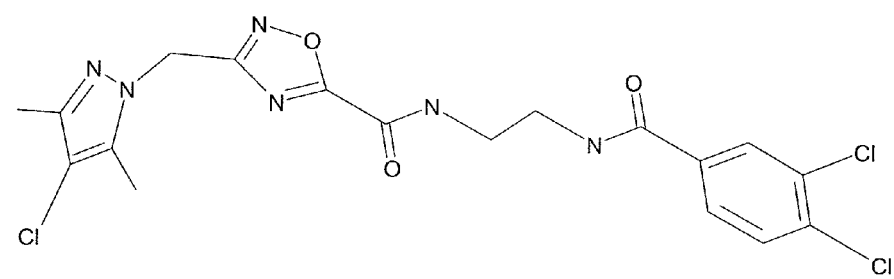
Figure 9:
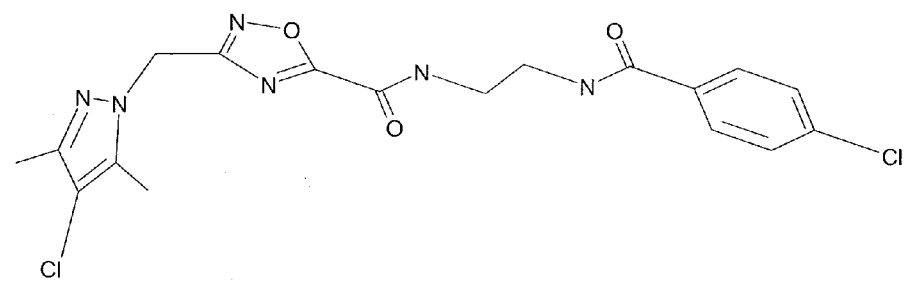
Figure 9:
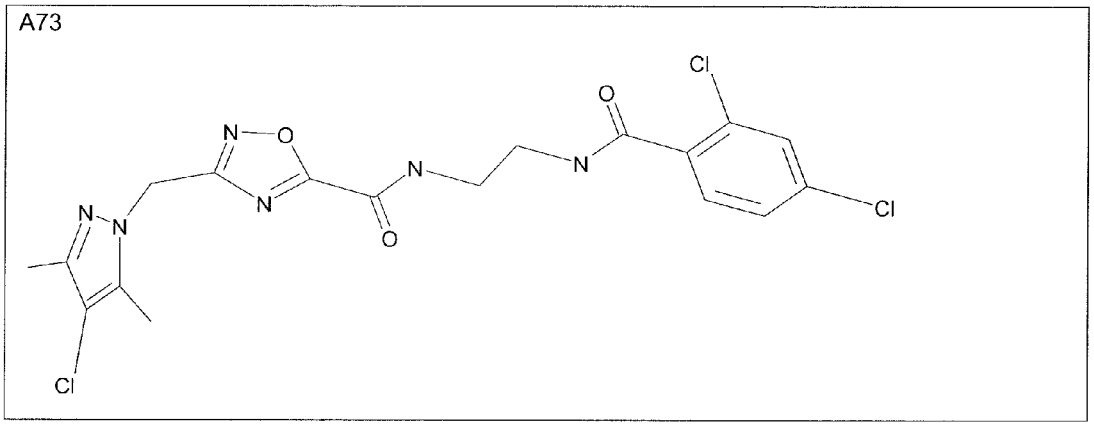
Figure 9:
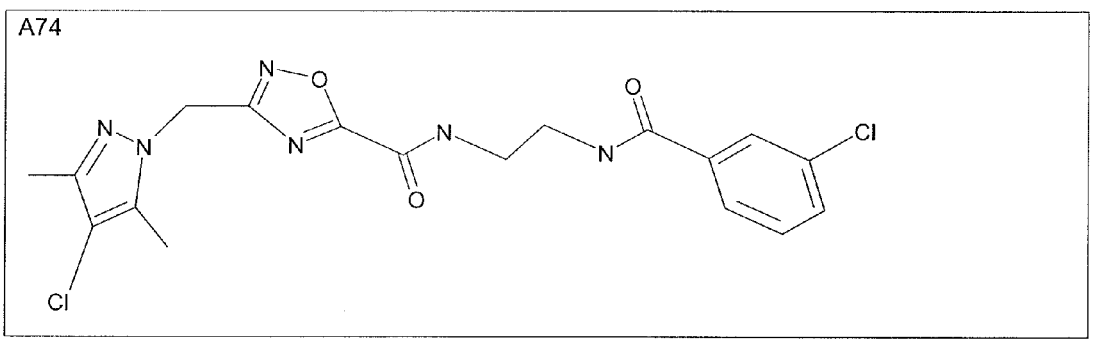
Figure 9:
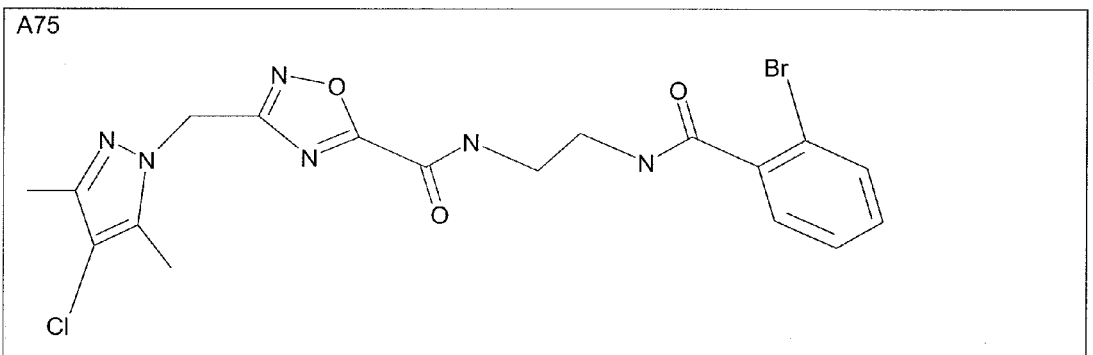
Figure 9:
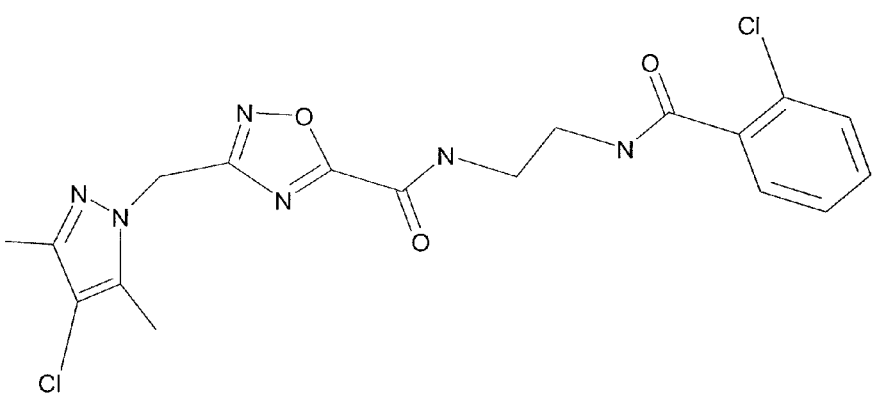
Figure 9:
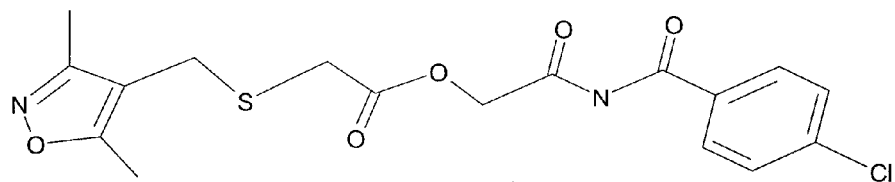
Figure 9:
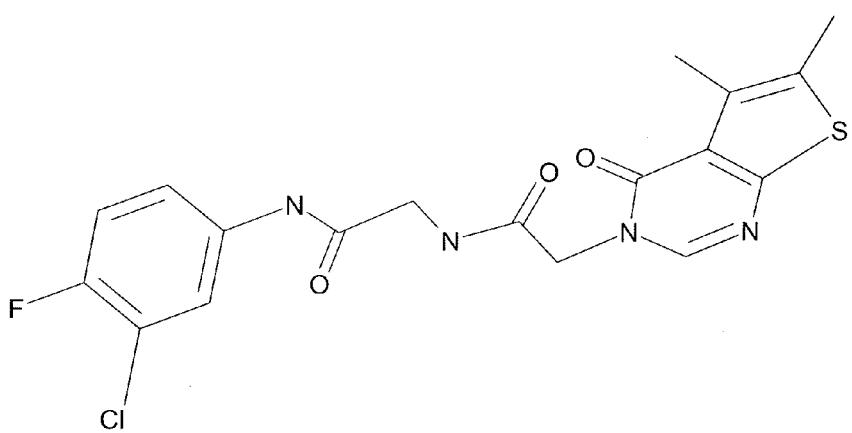
Figure 9:
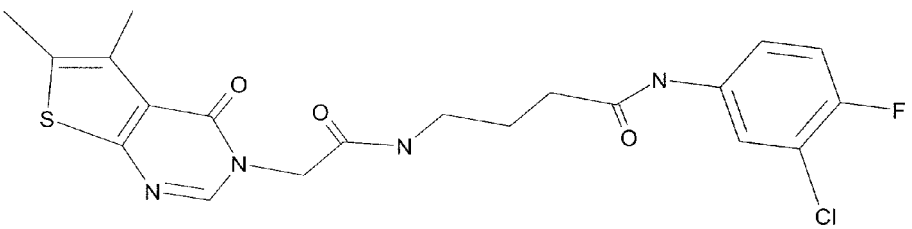
Figure 9:
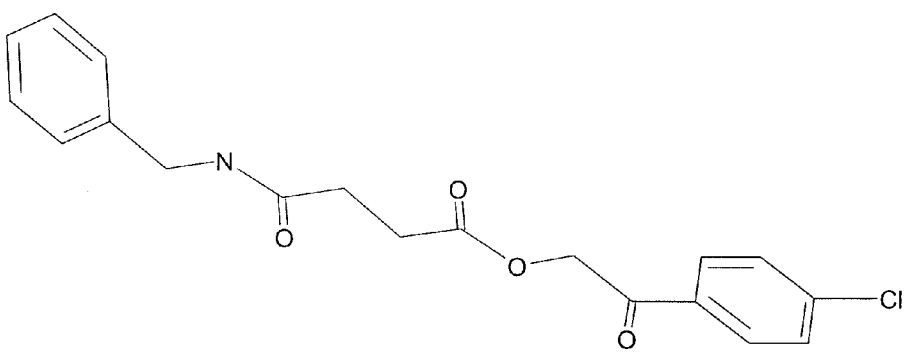
Figure 9:
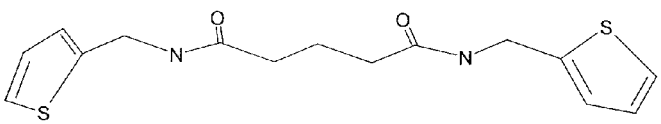
Figure 9:
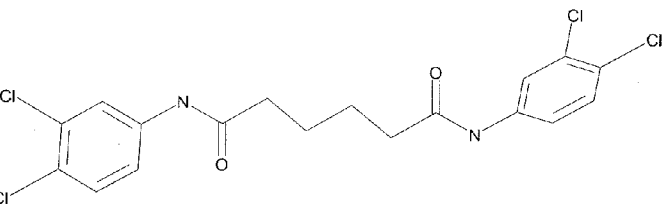
Figure 9:
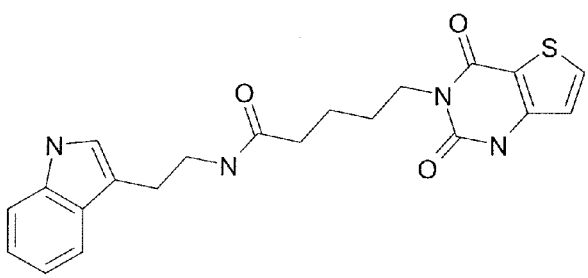
Figure 9:
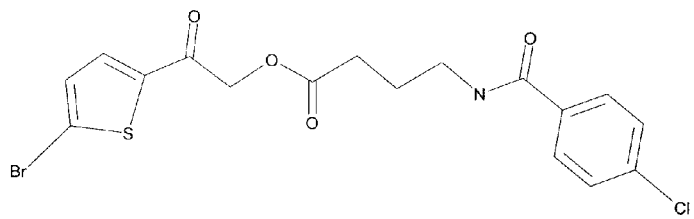
Figure 9:
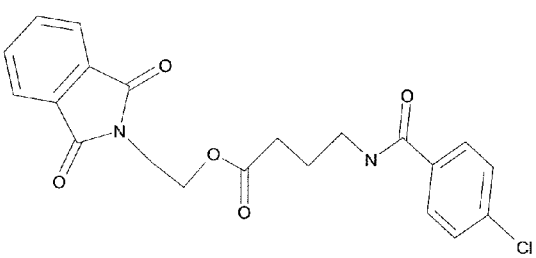
Figure 9:
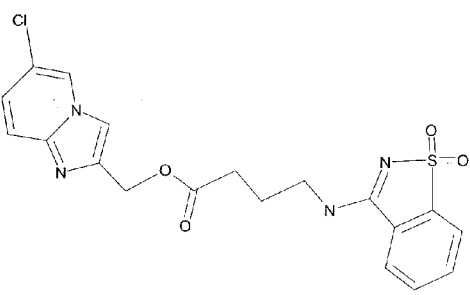
Figure 9:
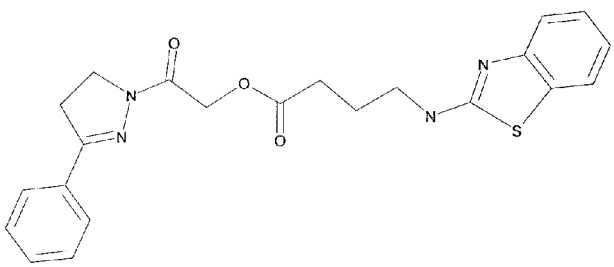
Figure 9:
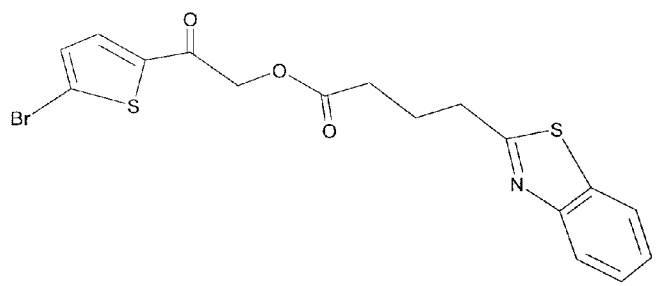
Figure 9:
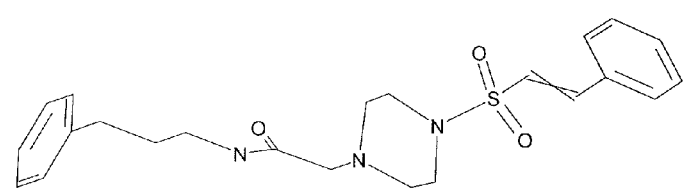
Figure 9:
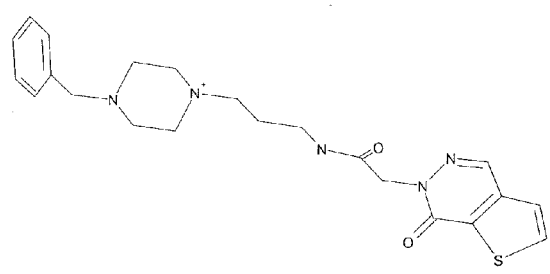
Figure 9:
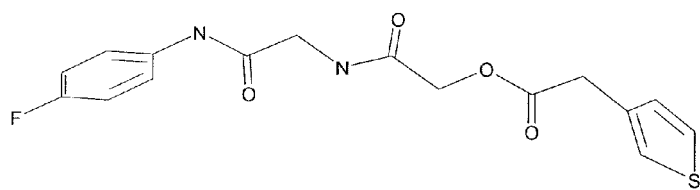
Figure 9:
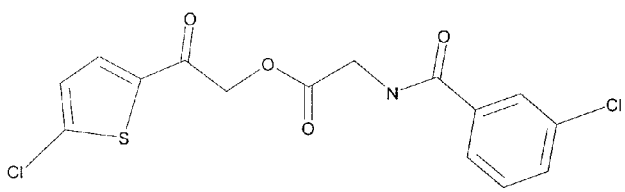
Figure 9:
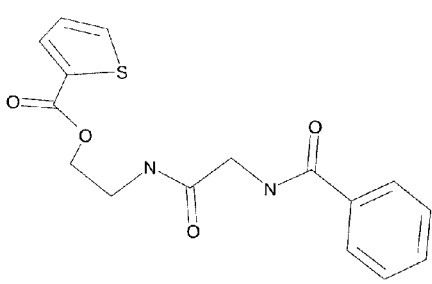
Figure 9:
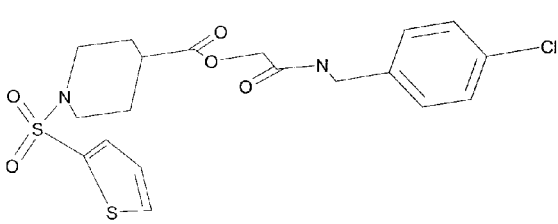
Figure 9:
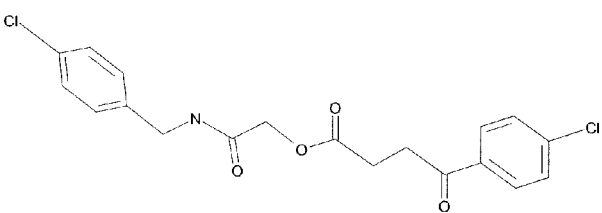
Figure 9:
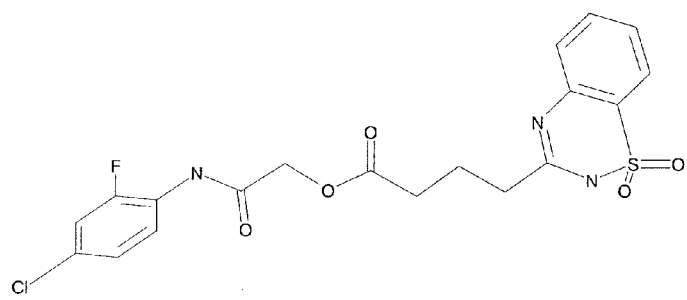
Figure 9:
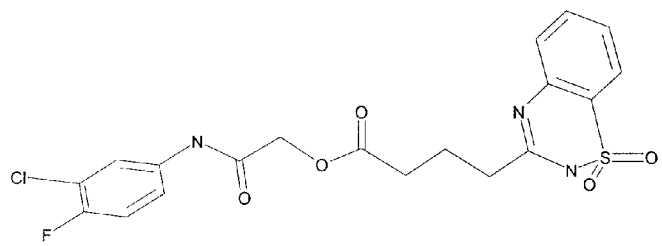
Figure 9:
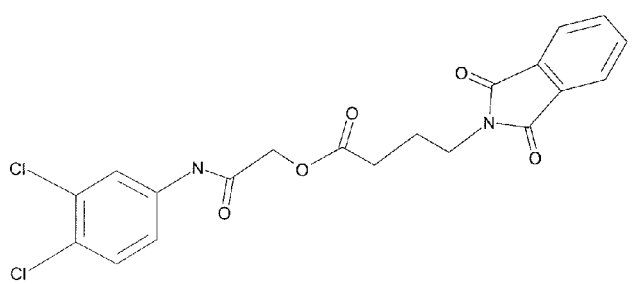
Figure 9:
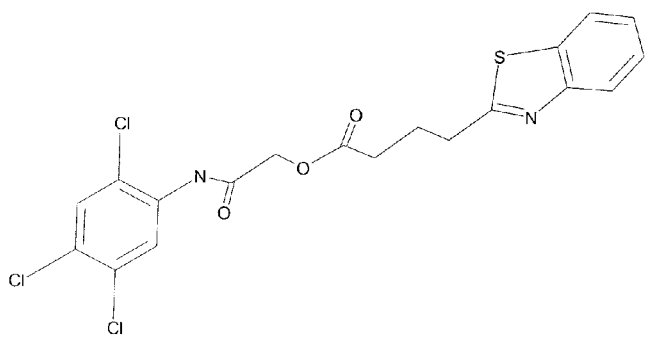
Figure 9:
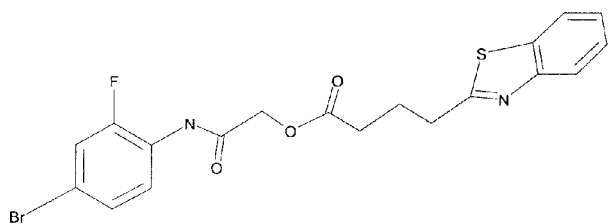
Figure 9:
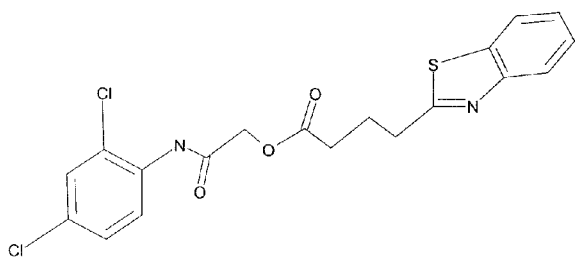
Figure 9:
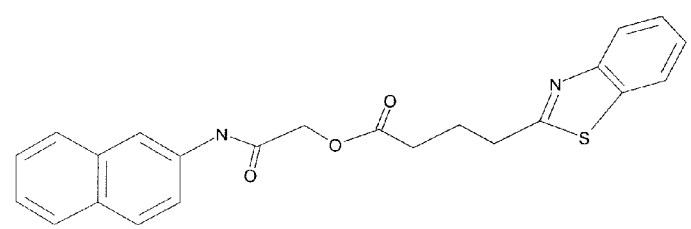
Figure 9:
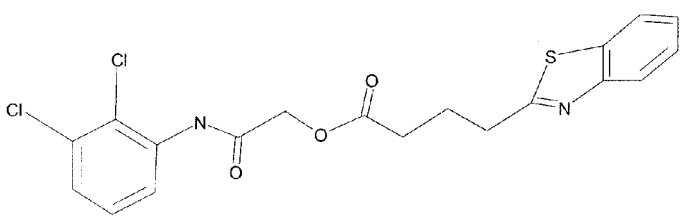
Figure 9:
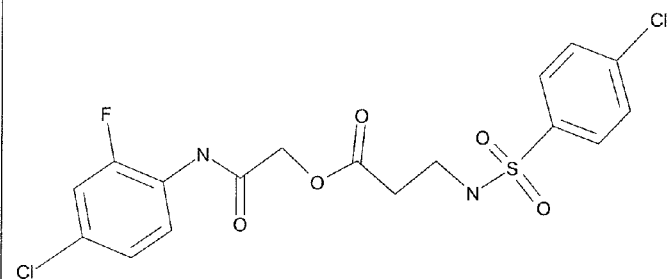
Figure 9:
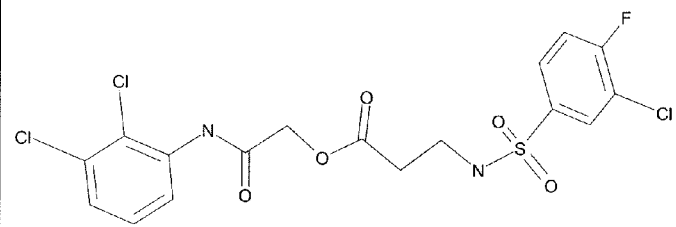
Figure 9:
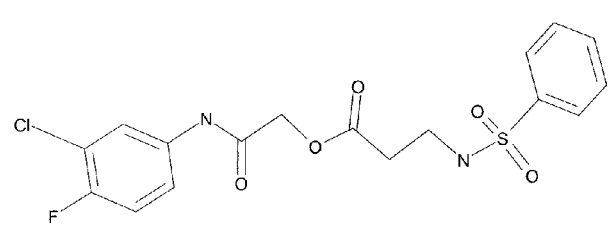
Figure 9:
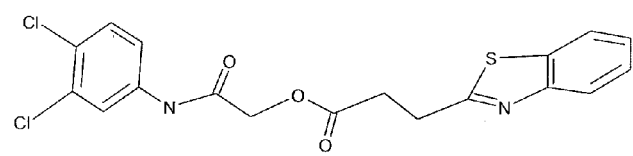
Figure 9:
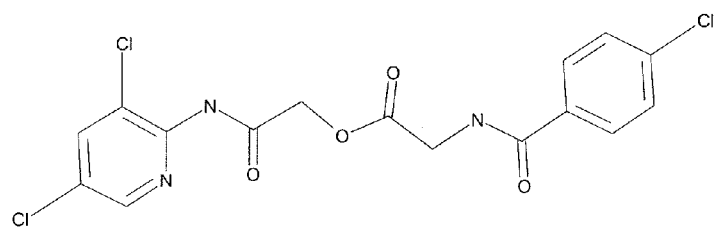
Figure 9:
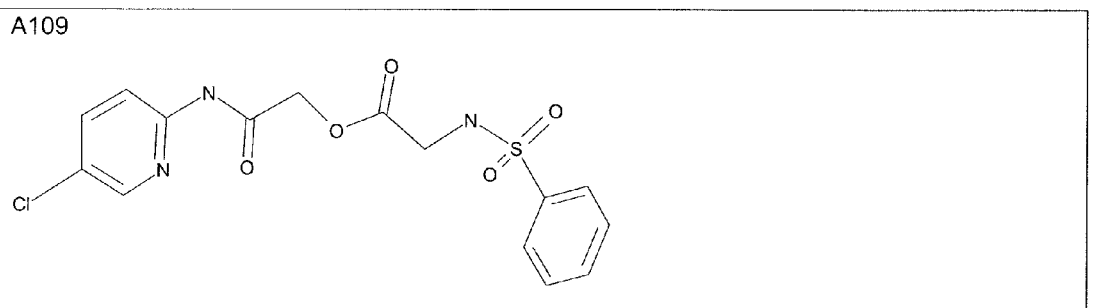
Figure 9:
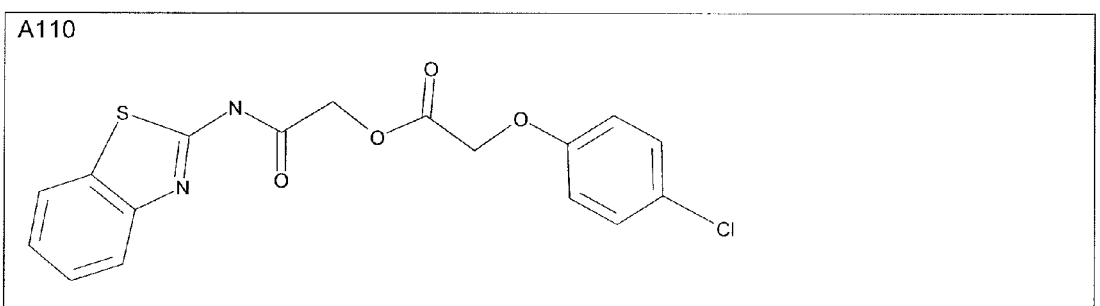
Figure 9:
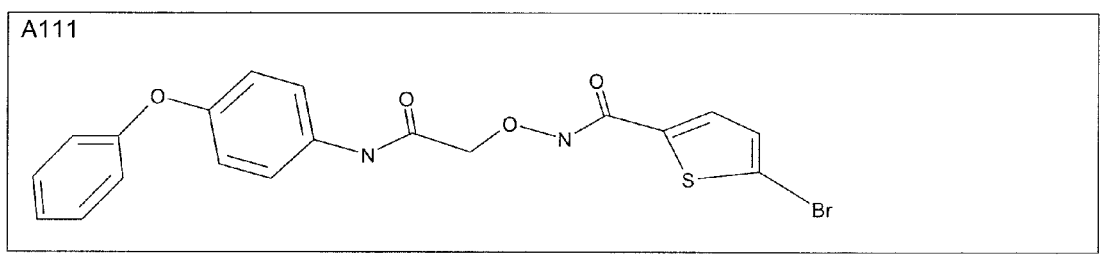
Figure 9:
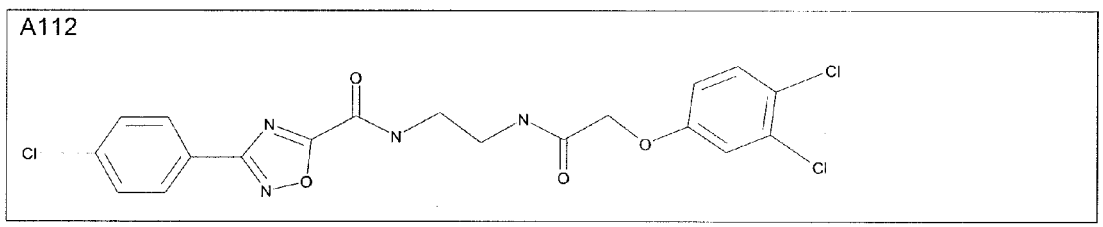
Figure 9:
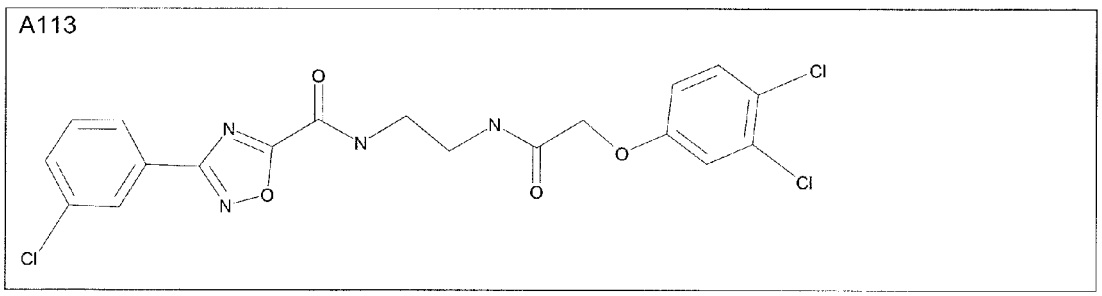
Figure 9:
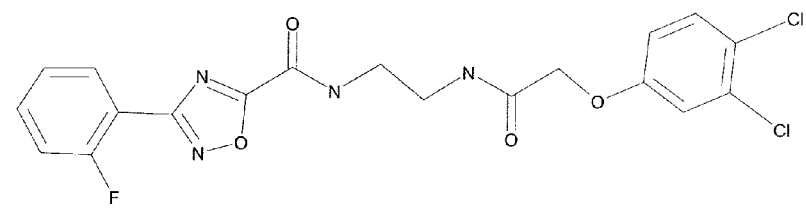
Figure 9:
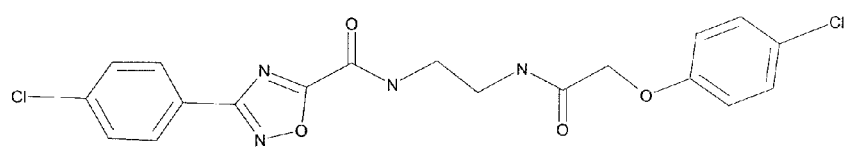
Figure 9:
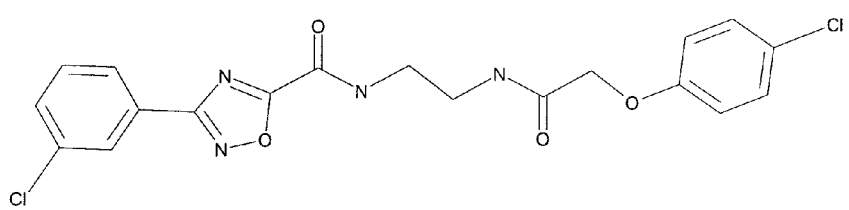
Figure 9:
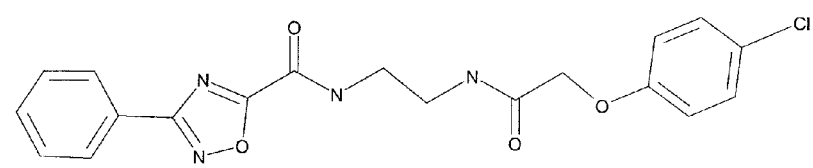
Figure 9:
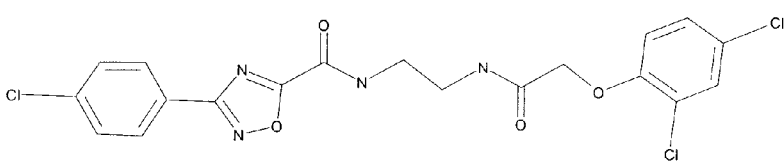
Figure 9:
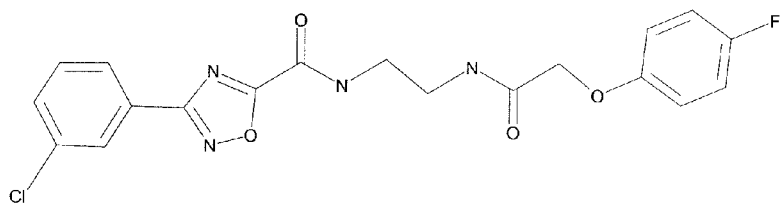
Figure 9:
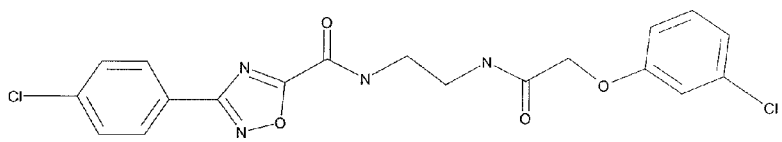
Figure 9:
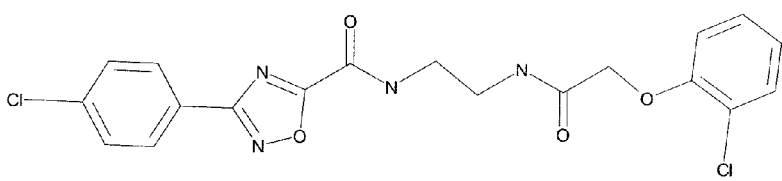
Figure 9:
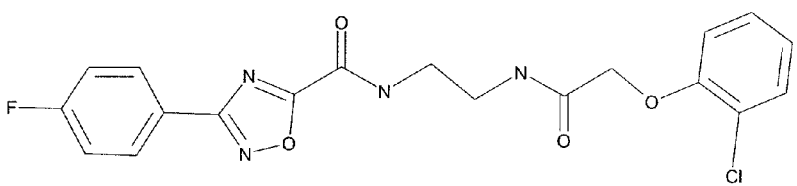
Figure 9:
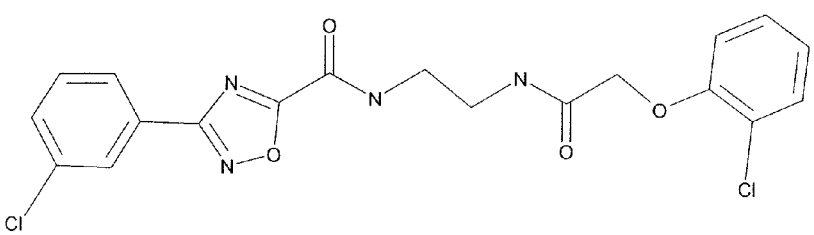
Figure 9:
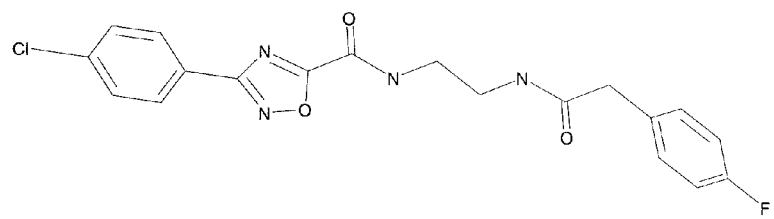
Figure 9:
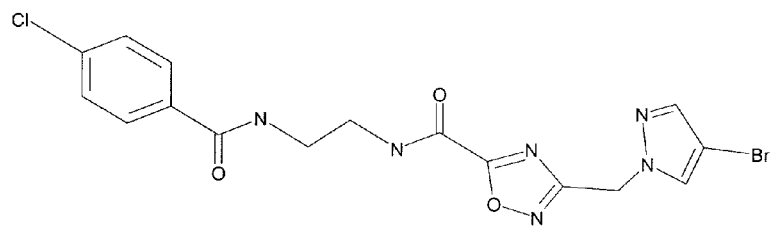
Figure 9:
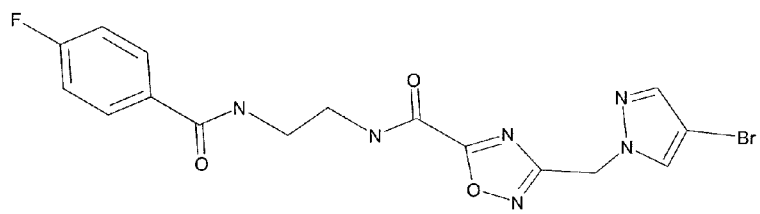
Figure 9:
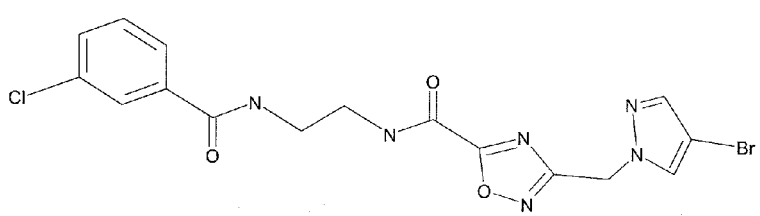
Figure 9:
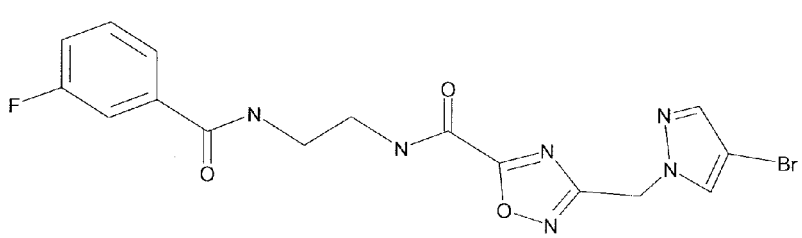
Figure 9:
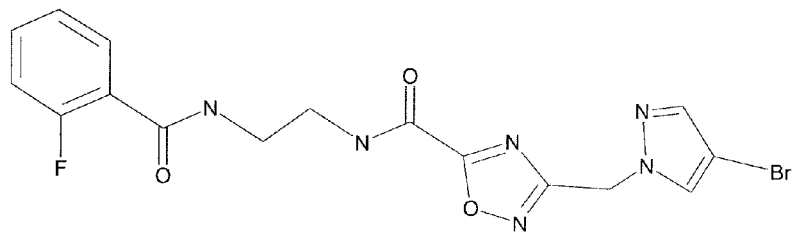
Figure 9:
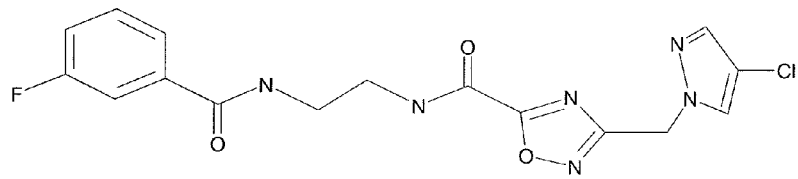
Figure 9:
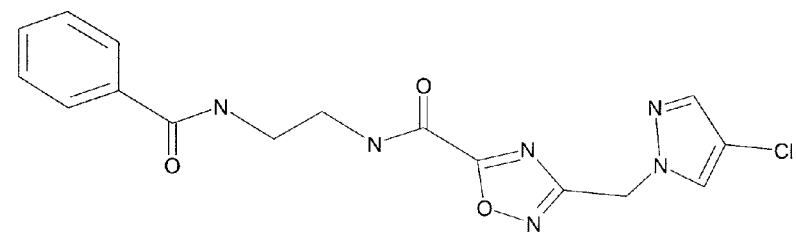
Figure 9:
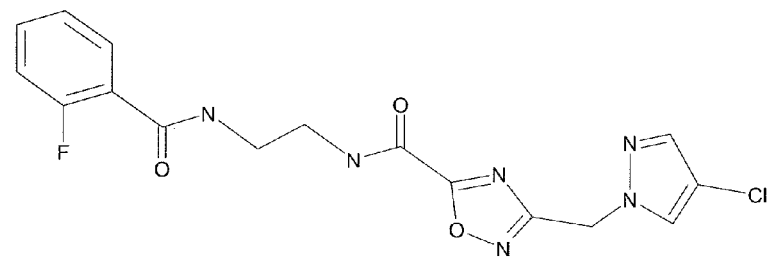
Figure 9:
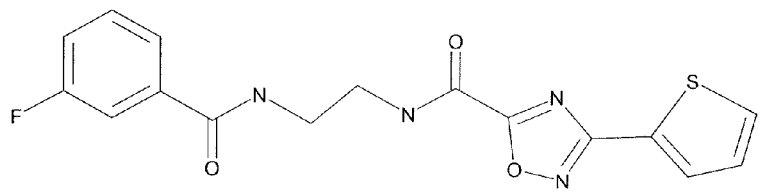
Figure 9:
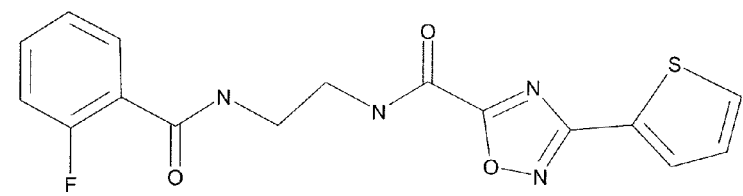
Figure 9:
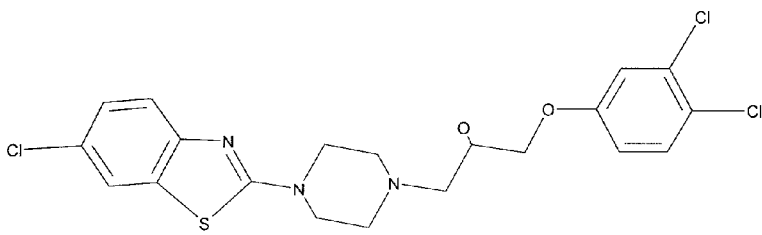
Figure 10:
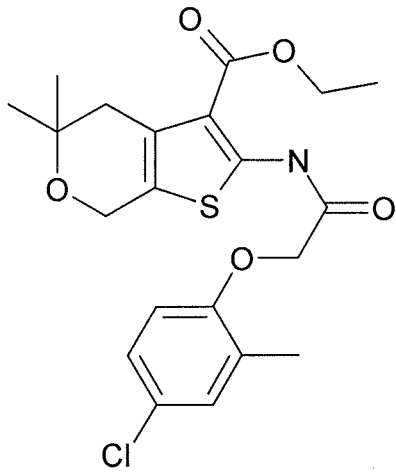
FIG. 10: A2 variants.
Figure 10:
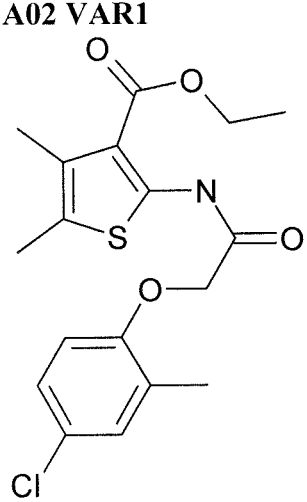
Figure 10:
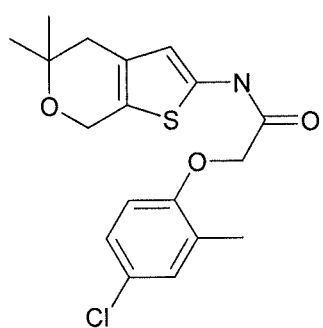
Figure 10:
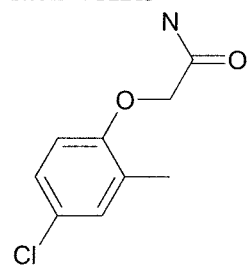
Figure 10:
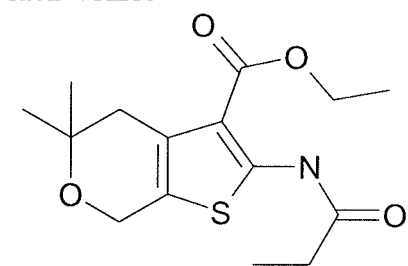
Figure 10:
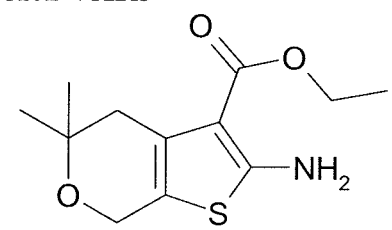
Figure 10:
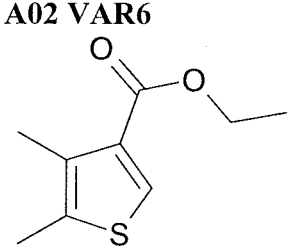
Figure 11:
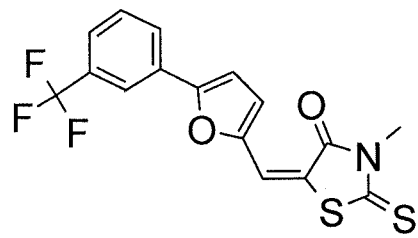
FIG. 11: A11/A12 variants.
Figure 11:
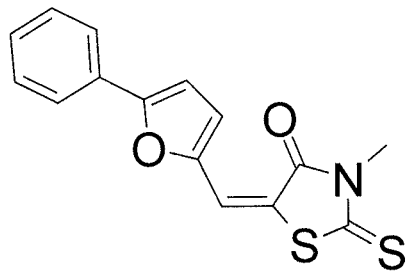
Figure 11:
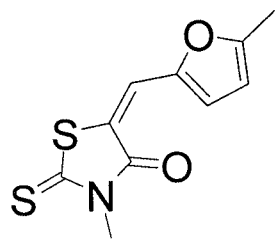
Figure 11:
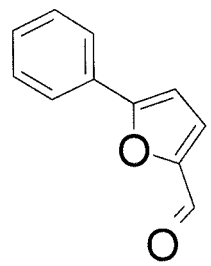
Figure 11:
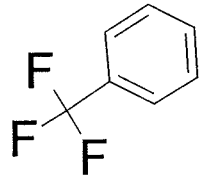
Figure 11:
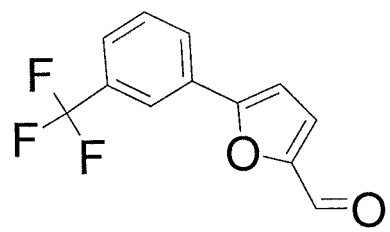
Figure 12:
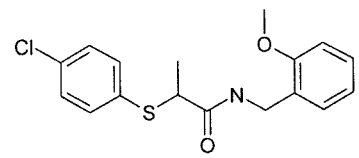
FIG. 12: A14 variants.
Figure 12:
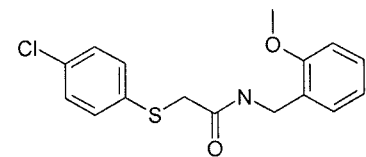
Figure 12:
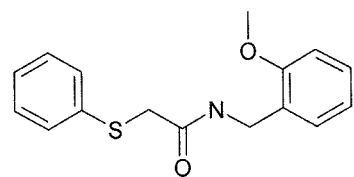
Figure 12:
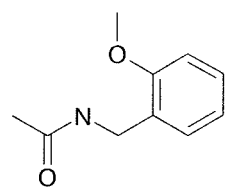
Figure 12:
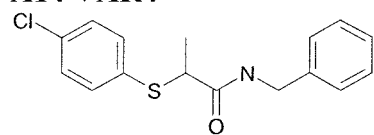
Figure 12:
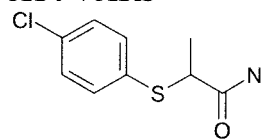

For lead optimization, an in silico screen was performed in order to find alternative molecules, based upon similarity, for the 88 activators of LR development. Similarity between molecules was assessed with a combination of shape-based screening with Spectrophore™- and Autophore-based classification algorithms. The in silico screen resulted in the identification of 135 unique compounds (FIG. 9) which are highly similar to the 88 initial activators.

Example 7

Figure 13:
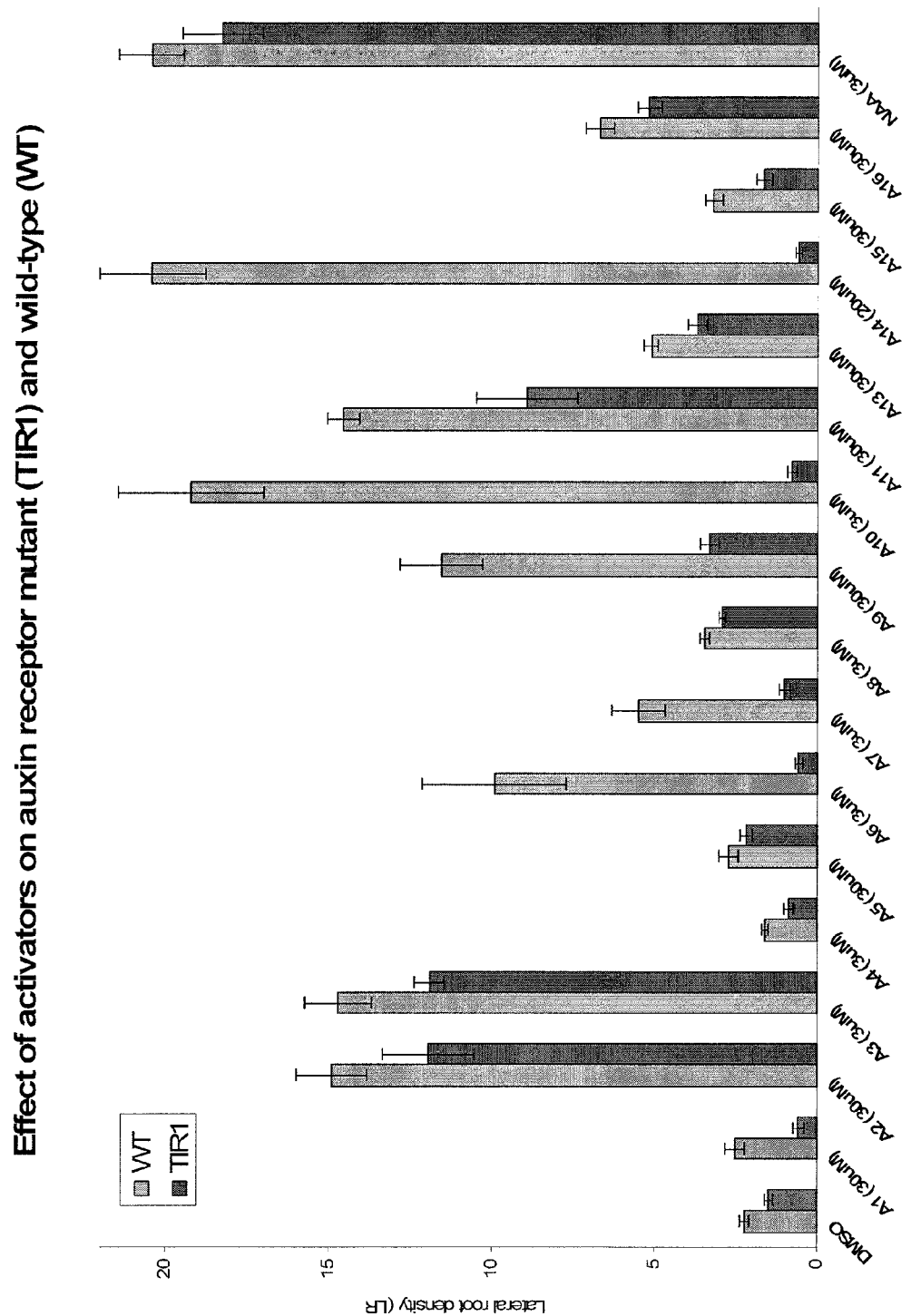
FIG. 13: Effect of activators on the auxin receptor mutant TIR1 compared with wild type.

Effect of Activators on the Auxin Receptor Mutant tir1 Compared with Wild Type The results are summarized in FIG. 13. From these results, it is evident that the working of the compounds A10 and A14 is strictly TIR1 dependent.

Example 8

Effect of A12 and NAA on Lateral Root Density and Root Length of Auxin Signaling Mutants For phenotypic analysis, all mutants were grown on vertically oriented square plates (Greiner Labortechnik, Austria) with solid medium derived from standard MS medium. The plates were put in a growth chamber under continuous light (110 µE.m2.s1 photosynthetically active radiation, supplied by cool-white fluorescent tungsten tubes; Osram) at 22° C. Three days after germination, the mutant plants were transferred to medium supplemented with compounds and were left to grow for another 7 days. After this, root length and number of lateral roots were counted using ImageJ 1.34 freeware.

The results are summarized in Table 1. DMSO is used as negative control.

TABLE 1 effect of A12 and NAA on lateral root density and root length of auxin signaling mutants
(DM: double mutant; tir TM: Tir1afb2afb3 triple mutant)

| | | Root length | | | LR density | |
| --- | --- | --- | --- | --- | --- | --- |
| | | | NAA | | | |
| | | A12 | (3 | | A12 | NAA |
| | DMSO | (30 uM) | uM) | DMSO | (30 uM) | (3 uM) |
| 1 Col-0 | 4.77 | 2.24 | 1.08 | 3.90 | | 52.98 |
| 2 Ws | 4.01 | 1.92 | 0.87 | 4.46 | 16.70 | 45.59 |
| 3 tir1-1 | 4.36 | 2.34 | 0.99 | 3.26 | 13.38 | 57.73 |
| 4 afb1-1 | 4.43 | 1.86 | 0.93 | 4.25 | 15.55 | 51.36 |
| 5 afb2-1 | 4.40 | 1.71 | 0.87 | 3.55 | 15.11 | 51.08 |
| 6 afb3-1 | 4.20 | 2.17 | 0.94 | 4.23 | 21.32 | 46.76 |
| 7 tir TM | 3.91 | 2.60 | 0.80 | 0.13 | 4.82 | 47.00 |
| 8 tir7-1 | 2.74 | 1.52 | 0.87 | 3.83 | 17.30 | 41.72 |
| 9 axr3-1 | — | — | — | — | — | — |
| 10 xbat32 | 5.67 | 2.44 | 1.33 | 2.82 | 14.16 | 36.83 |
| 11 lax3 | 5.01 | 2.48 | 1.02 | 3.49 | 15.27 | 63.09 |
| 12 msg2-1 | 4.72 | 1.58 | 1.13 | 3.60 | 27.49 | 37.22 |
| 13 axr5-1 | 5.08 | 3.40 | 1.27 | 3.81 | 14.10 | 27.56 |
| 14 slr-1 | 5.12 | 1.90 | 0.84 | 0.00 | 0.00 | 0.00 |
| arf7arf19 | | | | | | |
| 15 DM | 4.56 | 3.45 | 0.87 | 0.00 | 1.73 | — |
| 16 iaa28-1 | 4.22 | 3.39 | 0.86 | 1.21 | 8.85 | 48.10 |
| 17 aux1 | 5.31 | 2.24 | 0.93 | 3.88 | 15.94 | — |
| cyp79b2-3 | | | | | | |
| 18 DM | 4.70 | 2.26 | 1.43 | 4.53 | 17.30 | 37.27 |
| 19 axr1-12 | 4.90 | 1.62 | 1.12 | 3.47 | 15.84 | 40.22 |
| 20 CDKB DN | 3.58 | 1.56 | 0.42 | 1.20 | 9.09 | — |

TABLE 2 effect of activators on lateral root density of auxin signaling mutants (nd: not determined)

| | Afb1-1 | | Afb2-1 | | Afb3-1 | | Iaa28-1 | | Tir1-1 | | Tir7-1 | | TirTM | |
| --- | --- | --- | --- | --- | --- | --- | --- | --- | --- | --- | --- | --- | --- | --- |
| | LR/cm | SE | LR/cm | SE | LR/cm | SE | LR/cm | SE | LR/cm | SE | LR/cm | SE | LR/cm | SE |
| DMSO | 2.86 | 0.19 | 1.80 | 0.11 | 2.19 | 0.22 | 0.07 | 0.04 | 1.49 | 0.13 | 2.72 | 0.25 | 0.00 | 0.00 |
| A2 30 uM | 13.86 | 0.90 | 10.07 | 0.64 | 10.03 | 0.81 | 4.32 | 0.40 | 11.98 | 1.42 | 28.57 | 1.16 | 0.00 | 0.00 |
| A3 3 uM | 17.77 | 1.13 | 19.58 | 0.94 | 17.45 | 0.87 | 13.96 | 2.07 | 11.91 | 0.47 | 26.15 | 1.97 | 10.88 | 1.02 |
| A4 3 uM | 2.69 | 0.26 | 2.16 | 0.21 | 2.55 | 0.53 | 0.00 | 0.00 | 0.89 | 0.14 | 3.69 | 0.35 | 0.00 | 0.00 |
| A6 3 uM | 10.89 | 1.09 | 7.34 | 0.88 | 14.40 | 2.32 | 0.00 | 0.00 | 0.57 | 0.14 | 11.42 | 2.49 | 0.00 | 0.00 |
| A7 3 uM | 9.46 | 1.06 | 2.69 | 0.60 | 17.43 | 1.75 | 0.00 | 0.00 | 1.01 | 0.17 | 5.73 | 1.16 | 0.00 | 0.00 |
| A9 30 uM | 13.57 | 2.72 | 11.19 | 1.02 | 16.77 | 1.94 | 12.33 | 1.21 | 3.29 | 0.26 | 17.91 | 3.06 | 0.00 | 0.00 |
| A10 3 uM | 11.79 | 1.60 | 15.90 | 1.82 | 17.08 | 1.88 | 0.00 | 0.00 | 0.77 | 0.15 | 8.49 | 1.11 | 0.00 | 0.00 |
| A11 30 uM | 20.74 | 1.12 | 14.04 | 1.13 | 12.99 | 0.47 | 10.36 | 1.10 | 8.95 | 1.65 | 43.59 | 3.71 | 0.00 | 0.00 |
| A12 30 uM | 23.19 | 1.43 | 10.44 | 1.01 | 21.05 | 1.92 | 10.00 | 1.31 | nd | nd | 27.42 | 2.20 | 0.00 | 0.00 |

TABLE 2-continued effect of activators on lateral root density of auxin signaling mutants (nd: not determined)

| | | | | | | | | | | | | | |
|---|---|---|---|---|---|---|---|---|---|---|---|---|---|
| A14 30 uM | 24.29 | 2.09 | 22.38 | 1.22 | 30.09 | 1.59 | 20.71 | 1.29 | 0.52 | 0.09 | 33.41 | 4.92 | 0.00 | 0.00 |
| NAA 0.1 uM | 13.49 | 0.62 | 14.57 | 0.53 | 15.27 | 0.92 | 3.57 | 0.18 | 5.14 | 0.19 | 15.76 | 0.68 | 8.04 | 0.44 |
| NAA 0.3 uM | 8.76 | 0.70 | 8.98 | 0.88 | 8.93 | 0.95 | 7.46 | 0.44 | 11.34 | 0.74 | 5.78 | 0.52 | 18.89 | 1.64 |
| NAA 1 uM | 21.43 | 0.97 | 28.72 | 1.22 | 27.72 | 1.26 | 11.92 | 0.81 | 6.74 | 0.60 | 14.79 | 1.06 | 15.81 | 1.09 |
| NAA 3 uM | 47.81 | 1.98 | 59.72 | 4.59 | 55.01 | 2.87 | 40.09 | 2.43 | 18.30 | 1.24 | 46.33 | 6.74 | 45.09 | 7.81 |

| | Cyp79 | | Xbat32 | | Arf16 | | Arf17 | | Arf7Arf19 | | Axrt-12 | |
|---|---|---|---|---|---|---|---|---|---|---|---|---|
| | LR/cm | SE | LR/cm | SE | LR/cm | SE | LR/cm | SE | LR/cm | SE | LR/cm | SE |
| DMSO | 2.72 | 0.20 | 1.18 | 0.14 | 1.87 | 0.13 | 2.55 | 0.11 | 0.00 | 0.00 | 2.05 | 0.16 |
| A2 30 uM | 13.69 | 1.20 | 9.67 | 0.39 | 9.56 | 0.43 | 8.67 | 0.74 | 0.00 | 0.00 | 13.97 | 1.15 |
| A3 3 uM | 21.24 | 1.46 | 13.07 | 1.14 | 11.32 | 0.76 | 13.31 | 0.96 | 33.59 | 2.26 | 15.77 | 1.28 |
| A4 3 uM | 2.64 | 0.31 | 0.91 | 0.13 | 1.99 | 0.31 | 1.87 | 0.18 | 0.00 | 0.00 | 1.64 | 0.14 |
| A6 3 uM | 31.92 | 5.38 | 10.08 | 3.10 | 6.67 | 0.81 | 7.24 | 0.57 | 0.00 | 0.00 | 4.78 | 0.21 |
| A7 3 uM | 19.35 | 5.11 | 1.23 | 0.06 | 2.71 | 0.61 | 3.40 | 0.75 | 0.00 | 0.00 | 2.02 | 0.38 |
| A9 30 uM | 13.29 | 1.49 | 8.43 | 1.13 | 6.67 | 0.41 | 12.86 | 1.54 | 0.25 | 0.10 | 6.09 | 0.57 |
| A10 3 uM | 33.08 | 6.48 | 8.37 | 3.54 | 19.95 | 1.35 | 10.80 | 1.54 | 0.00 | 0.00 | 7.90 | 1.65 |
| A11 30 uM | 13.74 | 1.10 | 7.76 | 0.52 | 8.76 | 0.80 | 11.04 | 0.77 | 0.04 | 0.04 | 12.26 | 0.32 |
| A12 30 uM | 22.76 | 0.88 | nd | nd | 10.94 | 0.75 | 15.09 | 1.14 | 0.94 | 0.48 | 14.15 | 0.90 |
| A14 30 uM | 33.25 | 1.76 | 10.88 | 0.63 | 32.75 | 0.96 | 32.68 | 1.74 | 0.00 | 0.00 | 34.01 | 1.10 |
| NAA 0.1 uM | 15.83 | 0.59 | 4.27 | 0.19 | 8.05 | 0.66 | 6.57 | 0.42 | 0.00 | 0.00 | 8.04 | 0.44 |
| NAA 0.3 uM | 6.85 | 0.55 | 9.26 | 0.26 | 6.63 | 0.39 | 10.34 | 1.55 | 0.00 | 0.00 | 9.25 | 0.64 |
| NAA 1 uM | 22.20 | 1.53 | 12.70 | 0.48 | 10.83 | 0.46 | 0.47 | 0.62 | 0.17 | 0.17 | 9.03 | 0.34 |
| NAA 3 uM | 50.78 | 5.11 | 33.67 | 0.97 | 17.17 | 0.67 | 24.68 | 2.18 | 13.18 | 1.56 | 27.55 | 1.36 |

REFERENCES

Bennett M J, Marchant A, Green H G, May S T, Ward S P, Millner P A, Walker A R, Schulz B, Feldmann K A. (1996). *Arabidopsis* AUX1 gene: a permease-like regulator of root gravitropism. *Science.* 16;273(5277):948-50.

Casimiro, I., Marchant, A., Bhalerao, R. P., Beeckman, T., Dhooge, S., Swarup, R., Graham, N., Inze, D., Sandberg, G., Casero, P. J. and Bennett, M. (2001) Auxin transport promotes *Arabidopsis* lateral root initiation. *Plant Cell* 13(4):843-52.

Casimiro, I., Beeckman, T., Graham, N., Bhalerao, R., Zhang, H., Casero, P., Sandberg, G. and Bennett, M. J. (2003) Dissecting *Arabidopsis* lateral root development. *Trends Plant Sci* 8(4):165-71.

Collett C E, Harberd N P, Leyser O. (2002). Hormonal interactions in the control of *Arabidopsis* hypocotyl elongation. *Plant Physiol.* 124(2):553-62

Dai, X., Hayashi, K., Nozaki, H., Cheng, Y. and Zhao, Y. (2005) Genetic and chemical analyses of the action mechanisms of sirtinol in *Arabidopsis. Proc Natl Acad Sci USA* 102(8):3129-34.

Dharmasiri N, Dharmasiri S, Weijers D, Lechner E, Yamada M, Hobbie L, Ehrismann J S, Jurgens G, Estelle M. (2005). Plant development is regulated by a family of auxin receptor F box proteins. *Dev Cell.* 9(1):109-19.

Fleming, A. J. (2005) Formation of primordia and phyllotaxy. *Curr Opin Plant Biol* 8(1):53-8.

Fukaki H, Tameda S, Masuda H, Tasaka M. (2002). Lateral root formation is blocked by a gain-of-function mutation in the SOLITARY-ROOT/IAA14 gene of *Arabidopsis. Plant J.* 29(2):153-68.

Fukaki H, Nakao Y, Okushima Y, Theologis A, Tasaka M. (2005). Tissue-specific expression of stabilized SOLITARY-ROOT/IAA14 alters lateral root development in *Arabidopsis. Plant J.* 44(3):382-95.

Himanen, K., Boucheron, E., Vanneste, S., de Almeida Engler, J., Inze, D. and Beeckman, T. (2002) Auxin-mediated cell cycle activation during early lateral root initiation. *Plant Cell* 14(10):2339-51.

Kepinski, S. and Leyser, O. (2004) Auxin-induced SCFTIR1-Aux/IAA interaction involves stable modification of the SCFTIR1 complex. *Proc Natl Acad Sci USA* 101(33):12381-6.

Kepinski, S. and Leyser, O. (2005) The *Arabidopsis* F-box protein TIR1 is an auxin receptor. *Nature* 435(7041):446-51.

Ljung K, Hull A K, Celenza J, Yamada M, Estelle M, Normanly J, Sandberg G. (2005). Sites and regulation of auxin biosynthesis in *Arabidopsis* roots. *Plant Cell.* 17(4):1090-104.

Nodzon L A, Xu W H, Wang Y, Pi L Y, Chakrabarty P K, Song W Y. (2004). The ubiquitin ligase XBAT32 regulates lateral root development in *Arabidopsis. Plant J.* 40(6):996-1006.

Rogg L E, Lasswell J, Bartel B. (2001). A gain-of-function mutation in IAA28 suppresses lateral root development. *Plant Cell.* 13(3):465-80.

Ruegger M, Dewey E, Hobbie L, Brown D, Bernasconi P, Turner J, Muday G, Estelle M. (1997). Reduced naphthylphthalamic acid binding in the tir3 mutant of *Arabidopsis* is associated with a reduction in polar auxin transport and diverse morphological defects. *Plant Cell.* 9(5):745-57.

Ruegger M, Dewey E, Gray W M, Hobbie L, Turner J, Estelle M. (1998). The TIR1 protein of *Arabidopsis* functions in auxin response and is related to human SKP2 and yeast grr1p. *Genes Dev.* 12(2):198-207.

Teale, W. D., Paponov, I. A. and Palme, K. (2006) Auxin in action: signalling, transport and the control of plant growth and development. *Nat Rev Mol Cell Biol doi:*10.1038/nrm2020.

Timpte C, Lincoln C, Pickett F B, Turner J, Estelle M. (1995). The AXR1 and AUX1 genes of *Arabidopsis* function in separate auxin-response pathways. Plant J. 8(4):561-9.

Weiss, J., Delagado-Benarroch, L. and Egea-Cortines, M. (2005) Genetic control of floral size and proportions. *Int J Dev Biol* 49(5-6):513-25.

The invention claimed is:

1. A method of promoting lateral root growth in a plant having roots, the method comprising:
    applying a chemical compound selected from the group consisting of 3-methyl-2-thioxo-5-({5-[3-(trifluoromethyl)phenyl]-2-furyl}methylene)-1,3-thiazolidin-4-one, and 5-[3-(trifluoromethyl)phenyl]-2-furaldehyde thiosemicarbazone to the plant to promote lateral root growth.

2. A method of promoting lateral root growth in a plant having roots, the method comprising:
    applying a chemical compound wherein the chemical compound has the structure

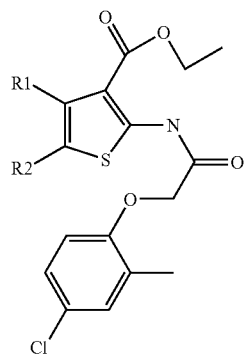

wherein R1 is H, methyl, ethyl, propyl, butyl or isobutyl and R2 is H, methyl or hydroxymethyl, or R1 and R2 form a closed ring with the structure —CH$_2$—C—(CH$_3$)$_2$—O—CH$_2$— to the plant to promote lateral root growth.

3. A method of promoting lateral root growth in a plant having roots, the method comprising:
    applying a chemical compound wherein the chemical compound has a structure

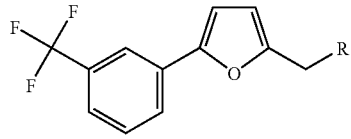

wherein R is selected from the group consisting of carbonyl, thiosemicarbazone and 5-methylene-1,3-thiazolidin-4-one, to the plant to promote lateral root growth.

4. The method according to claim 3, wherein the chemical compound comprises at least one of the following compounds:

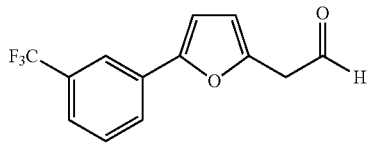

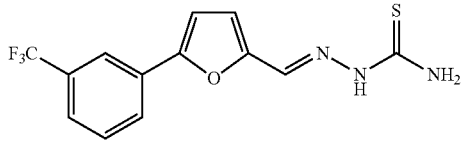

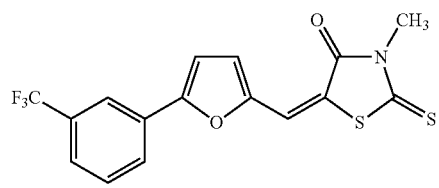

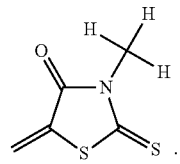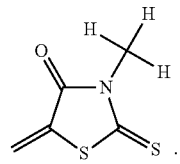

* * * * *

SEQUENCE LISTING

<160> NUMBER OF SEQ ID NOS: 32

<210> SEQ ID NO 1
<211> LENGTH: 24
<212> TYPE: DNA
<213> ORGANISM: Artificial
<220> FEATURE:
<223> OTHER INFORMATION: Forward primer CDKA1;1

<400> SEQUENCE: 1
attgcgtatt gccactctca tagg         24

<210> SEQ ID NO 2
<211> LENGTH: 22
<212> TYPE: DNA
<213> ORGANISM: Artificial
<220> FEATURE:
<223> OTHER INFORMATION: CDKA1;1 reverse primer

<400> SEQUENCE: 2
tcctgacagg gataccgaat gc         22

<210> SEQ ID NO 3
<211> LENGTH: 22
<212> TYPE: DNA
<213> ORGANISM: Artificial
<220> FEATURE:
<223> OTHER INFORMATION: EEF1a4 forward primer

<400> SEQUENCE: 3
ctggaggttt tgaggctggt at         22

<210> SEQ ID NO 4
<211> LENGTH: 21
<212> TYPE: DNA
<213> ORGANISM: Artificial
<220> FEATURE:
<223> OTHER INFORMATION: EEF1a4 reverse primer

<400> SEQUENCE: 4
ccaagggtga aagcaagaag a         21

<210> SEQ ID NO 5
<211> LENGTH: 24
<212> TYPE: DNA
<213> ORGANISM: Artificial
<220> FEATURE:
<223> OTHER INFORMATION: CYP79B3 forward primer

<400> SEQUENCE: 5
aaagtcatct tcacgaaaca agaa         24

<210> SEQ ID NO 6
<211> LENGTH: 19
<212> TYPE: DNA
<213> ORGANISM: Artificial
<220> FEATURE:
<223> OTHER INFORMATION: CYP79B3 reverse primer

```
<400> SEQUENCE: 6
ttttaagcat cgccggaat                                                19

<210> SEQ ID NO 7
<211> LENGTH: 27
<212> TYPE: DNA
<213> ORGANISM: Artificial
<220> FEATURE:
<223> OTHER INFORMATION: CYP79B2 forward primer

<400> SEQUENCE: 7
aaactaaact acgtcaaagc tatcctc                                       27

<210> SEQ ID NO 8
<211> LENGTH: 18
<212> TYPE: DNA
<213> ORGANISM: Artificial
<220> FEATURE:
<223> OTHER INFORMATION: CYP79B2 reverse primer

<400> SEQUENCE: 8
acgtggggga ggttgaag                                                 18

<210> SEQ ID NO 9
<211> LENGTH: 19
<212> TYPE: DNA
<213> ORGANISM: Artificial
<220> FEATURE:
<223> OTHER INFORMATION: TIR1 forward primer

<400> SEQUENCE: 9
cctaaactgc agcgcctct                                                19

<210> SEQ ID NO 10
<211> LENGTH: 19
<212> TYPE: DNA
<213> ORGANISM: Artificial
<220> FEATURE:
<223> OTHER INFORMATION: TIR1 reverse primer

<400> SEQUENCE: 10
ggttgaagca agcacctca                                                19

<210> SEQ ID NO 11
<211> LENGTH: 21
<212> TYPE: DNA
<213> ORGANISM: Artificial
<220> FEATURE:
<223> OTHER INFORMATION: ABP1 forward primer

<400> SEQUENCE: 11
ttgcatggaa tgaaagaggt t                                             21

<210> SEQ ID NO 12
<211> LENGTH: 20
<212> TYPE: DNA
<213> ORGANISM: Artificial
<220> FEATURE:
<223> OTHER INFORMATION: ABP1 reverse primer

<400> SEQUENCE: 12
tgtctctgaa cctggagcaa                                               20

<210> SEQ ID NO 13
<211> LENGTH: 23
<212> TYPE: DNA
```

```
<213> ORGANISM: Artificial
<220> FEATURE:
<223> OTHER INFORMATION: ARF7 forward primer

<400> SEQUENCE: 13
agaaaatctt tcctgctctg gat                                              23

<210> SEQ ID NO 14
<211> LENGTH: 23
<212> TYPE: DNA
<213> ORGANISM: Artificial
<220> FEATURE:
<223> OTHER INFORMATION: ARF7 reverse primer

<400> SEQUENCE: 14
tgtctgaaag tccatgtgtt gtc                                              23

<210> SEQ ID NO 15
<211> LENGTH: 20
<212> TYPE: DNA
<213> ORGANISM: Artificial
<220> FEATURE:
<223> OTHER INFORMATION: IAA19 forward primer

<400> SEQUENCE: 15
gtggtgacgc tgagaaggtt                                                  20

<210> SEQ ID NO 16
<211> LENGTH: 20
<212> TYPE: DNA
<213> ORGANISM: Artificial
<220> FEATURE:
<223> OTHER INFORMATION: IAA19 reverse primer

<400> SEQUENCE: 16
cgtggtcgaa gcttccttac                                                  20

<210> SEQ ID NO 17
<211> LENGTH: 23
<212> TYPE: DNA
<213> ORGANISM: Artificial
<220> FEATURE:
<223> OTHER INFORMATION: PIN1 forward primer

<400> SEQUENCE: 17
tactccgaga ccttccaact acg                                              23

<210> SEQ ID NO 18
<211> LENGTH: 18
<212> TYPE: DNA
<213> ORGANISM: Artificial
<220> FEATURE:
<223> OTHER INFORMATION: PIN1 reverse primer

<400> SEQUENCE: 18
tccaccgcca ccacttcc                                                    18

<210> SEQ ID NO 19
<211> LENGTH: 24
<212> TYPE: DNA
<213> ORGANISM: Artificial
<220> FEATURE:
<223> OTHER INFORMATION: PIN3 forward primer

<400> SEQUENCE: 19
gagggagaag gaagaaaggg aaac                                             24
```

-continued

```
<210> SEQ ID NO 20
<211> LENGTH: 24
<212> TYPE: DNA
<213> ORGANISM: Artificial
<220> FEATURE:
<223> OTHER INFORMATION: PIN3 reverse primer

<400> SEQUENCE: 20
cttggcttgt aatgttggca tcag                                          24

<210> SEQ ID NO 21
<211> LENGTH: 22
<212> TYPE: DNA
<213> ORGANISM: Artificial
<220> FEATURE:
<223> OTHER INFORMATION: PIN4 forward primer

<400> SEQUENCE: 21
ttgtctctga tcaacctcga aa                                            22

<210> SEQ ID NO 22
<211> LENGTH: 20
<212> TYPE: DNA
<213> ORGANISM: Artificial
<220> FEATURE:
<223> OTHER INFORMATION: PIN4 reverse primer

<400> SEQUENCE: 22
atcaagaccg ccgatatcat                                               20

<210> SEQ ID NO 23
<211> LENGTH: 22
<212> TYPE: DNA
<213> ORGANISM: Artificial
<220> FEATURE:
<223> OTHER INFORMATION: LAX3 forward primer

<400> SEQUENCE: 23
ttacctttgc tcctgctcct tc                                            22

<210> SEQ ID NO 24
<211> LENGTH: 22
<212> TYPE: DNA
<213> ORGANISM: Artificial
<220> FEATURE:
<223> OTHER INFORMATION: LAX3 reverse primer

<400> SEQUENCE: 24
atccatcctc ctaccactct cg                                            22

<210> SEQ ID NO 25
<211> LENGTH: 23
<212> TYPE: DNA
<213> ORGANISM: Artificial
<220> FEATURE:
<223> OTHER INFORMATION: AUX1 forward primer

<400> SEQUENCE: 25
agtagcaaat gacaacggaa cag                                           23

<210> SEQ ID NO 26
<211> LENGTH: 19
<212> TYPE: DNA
<213> ORGANISM: Artificial
<220> FEATURE:
<223> OTHER INFORMATION: AUX1 reverse primer
```

```
<400> SEQUENCE: 26
agagccaccg tgccatagg                                              19

<210> SEQ ID NO 27
<211> LENGTH: 21
<212> TYPE: DNA
<213> ORGANISM: Artificial
<220> FEATURE:
<223> OTHER INFORMATION: PLT1 forward primer

<400> SEQUENCE: 27
acgatatgcc ttccagtgat g                                           21

<210> SEQ ID NO 28
<211> LENGTH: 20
<212> TYPE: DNA
<213> ORGANISM: Artificial
<220> FEATURE:
<223> OTHER INFORMATION: PLT1 reverse primer

<400> SEQUENCE: 28
ttcagaccca ttccttgtgc                                             20

<210> SEQ ID NO 29
<211> LENGTH: 23
<212> TYPE: DNA
<213> ORGANISM: Artificial
<220> FEATURE:
<223> OTHER INFORMATION: CYCB1;1 forward primer

<400> SEQUENCE: 29
cctggtggag tggttgattg atg                                         23

<210> SEQ ID NO 30
<211> LENGTH: 23
<212> TYPE: DNA
<213> ORGANISM: Artificial
<220> FEATURE:
<223> OTHER INFORMATION: CYCB1;1 reverse primer

<400> SEQUENCE: 30
cgacatgaga agagcactga gac                                         23

<210> SEQ ID NO 31
<211> LENGTH: 25
<212> TYPE: DNA
<213> ORGANISM: Artificial
<220> FEATURE:
<223> OTHER INFORMATION: CYCD3;1 forward primer

<400> SEQUENCE: 31
ttcgttcgta gaccacatta tcagg                                       25

<210> SEQ ID NO 32
<211> LENGTH: 24
<212> TYPE: DNA
<213> ORGANISM: Artificial
<220> FEATURE:
<223> OTHER INFORMATION: CYCD3;1 reverse primer

<400> SEQUENCE: 32
cggagattac agagaggagg agac                                        24
```